United States Patent
Chen et al.

(10) Patent No.: US 10,688,080 B2
(45) Date of Patent: Jun. 23, 2020

(54) COMPOSITIONS, METHODS OF USE, AND METHODS OF TREATMENT

(71) Applicants: University of South Florida, Tampa, FL (US); The Regents of the University of California, Oakland, CA (US)

(72) Inventors: Yu Chen, Tampa, FL (US); Nicholas Joseph Torelli, Denver, CO (US); Orville Antonio Pemberton, Tampa, FL (US); Xiujun Zhang, Lutz, FL (US); Adam Renslo, San Francisco, CA (US); Kyle Defrees, San Francisco, CA (US); Priyadarshini Jaishankar, Newark, CA (US)

(73) Assignees: UNIVERSITY OF SOUTH FLORIDA, Tampa, FL (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/049,164

(22) Filed: Jul. 30, 2018

(65) Prior Publication Data
US 2018/0333390 A1    Nov. 22, 2018

Related U.S. Application Data

(63) Continuation-in-part of application No. PCT/US2017/020632, filed on Mar. 3, 2017.

(60) Provisional application No. 62/302,861, filed on Mar. 3, 2016.

(51) Int. Cl.
| | | |
|---|---|---|
| A61K 31/41 | (2006.01) |
| A61K 31/55 | (2006.01) |
| A61K 31/454 | (2006.01) |
| A61K 31/427 | (2006.01) |
| A61K 31/4155 | (2006.01) |
| A61K 45/06 | (2006.01) |
| A61P 31/04 | (2006.01) |
| C07D 417/14 | (2006.01) |
| C07D 403/12 | (2006.01) |
| C07D 401/12 | (2006.01) |
| C07D 403/14 | (2006.01) |
| C07D 257/06 | (2006.01) |

(52) U.S. Cl.
CPC .......... *A61K 31/41* (2013.01); *A61K 31/4155* (2013.01); *A61K 31/427* (2013.01); *A61K 31/454* (2013.01); *A61K 31/55* (2013.01); *A61K 45/06* (2013.01); *A61P 31/04* (2018.01); *C07D 257/06* (2013.01); *C07D 401/12* (2013.01); *C07D 403/12* (2013.01); *C07D 403/14* (2013.01); *C07D 417/14* (2013.01)

(58) Field of Classification Search
None
See application file for complete search history.

(56) References Cited

U.S. PATENT DOCUMENTS 5,432,179 A    7/1995 Kumagai

FOREIGN PATENT DOCUMENTS

WO    WO2013103760 A1    7/2013

OTHER PUBLICATIONS

"Pubchem CID 2163470" create date: Jul. 14, 2005 (Jul. 14, 2005) Date Accessed: Apr. 24, 2017 (Apr. 24, 2017); p. 4, ,compound listed, p. 12.
"Pubchem AID 485294" Create date: Sep. 29, 2010 (Sep. 29, 2010) Date Accessed: Apr. 24, 2017 (Apr. 24, 2017); p. 1, 3.
PCT/US2017/020632 International Search Report dated Jun. 30, 2017.

*Primary Examiner* — Anna Pagonakis
(74) *Attorney, Agent, or Firm* — Thomas | Horstemeyer, LLP

(57) ABSTRACT

The present disclosure provides compositions including a beta-lactamase inhibitor, pharmaceutical compositions including a beta-lactamase inhibitor, methods of treatment of a condition (e.g., infection) or disease, methods of treatment using compositions or pharmaceutical compositions, and the like.

16 Claims, No Drawings

COMPOSITIONS, METHODS OF USE, AND METHODS OF TREATMENT

CLAIM OF PRIORITY TO RELATED APPLICATION

This application is a Bypass Continuation of PCT Application entitled "Compositions, Methods Of Use, And Methods Of Treatment," having Serial Number PCT/US17/20632 and filed Mar. 3, 2017, and claims priority to U.S. Provisional Application Ser. No. 62/302,861 and filed Mar. 3, 2016, both of which are hereby incorporated herein by reference in their entireties.

NOTICE OF GOVERNMENT-SPONSORED RESEARCH

Government sponsorship notice: This invention was made with government support under Grant Number R01 AI103158 awarded by the National Institutes of Health/ National Institute of Allergy and Infectious Diseases. The government has certain rights in the invention.

BACKGROUND

Beta-lactam compounds such as penicillins are the most widely used antibiotics due to their effective inhibition of the transpeptidases required for bacterial cell wall synthesis. Beta-lactamases catalyze β-lactam hydrolysis and are primary mediators of bacterial resistance to these compounds. There are four β-lactamase families, Classes A to D, among which Classes A and C are the most commonly observed in the clinic. CTX-M is a new group of Class A β-lactamases that is particularly effective against the extended spectrum β-lactam antibiotics. The widespread emergence of extended spectrum beta-lactamase (ESBL) will continue to limit treatment options for bacterial infections. Thus, there is a need to address these issues.

SUMMARY

The present disclosure provides compositions including a beta-lactamase inhibitor, pharmaceutical compositions including a beta-lactamase inhibitor, methods of treatment of a condition (e.g., infection) or disease, methods of treatment using compositions or pharmaceutical compositions, and the like.

An embodiment of the present disclosure includes a composition, among others, that includes a beta-lactamase inhibitor having one of the following structures:

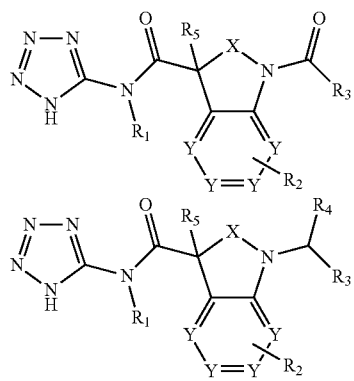

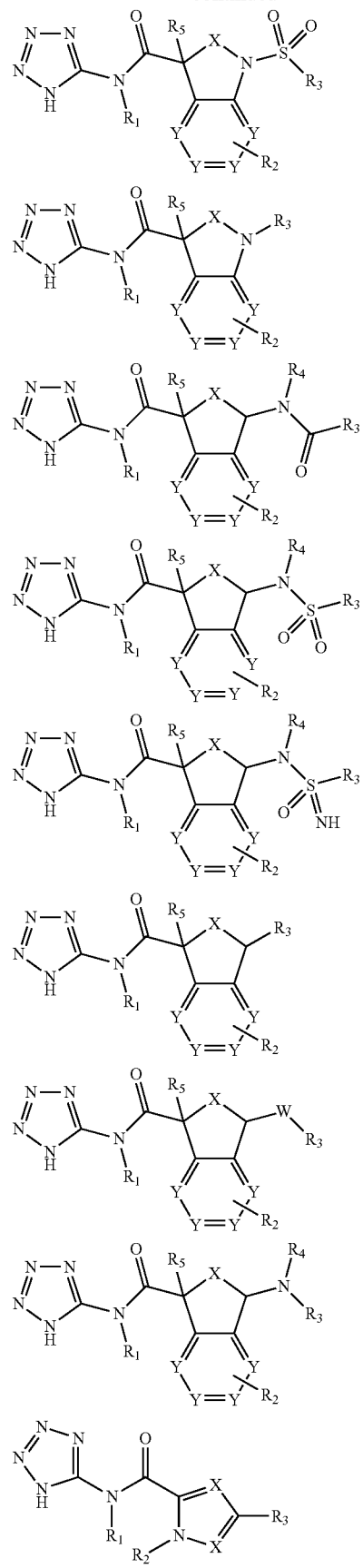

-continued
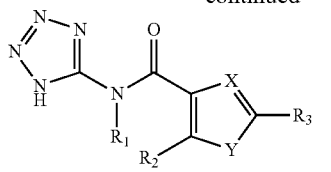
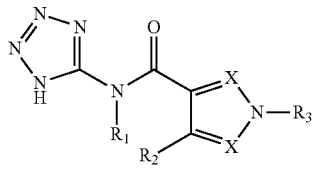
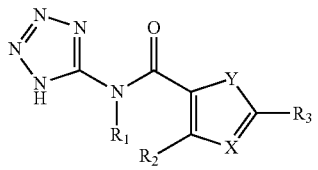
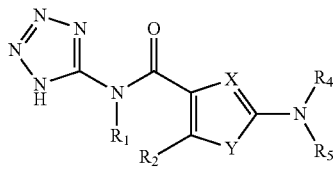
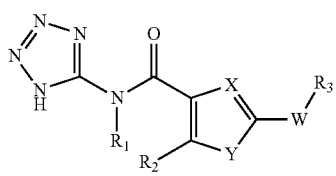
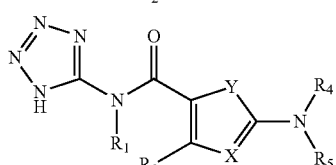
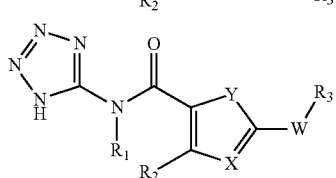
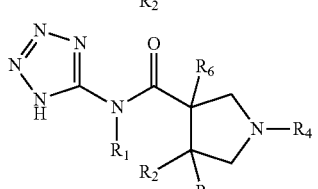
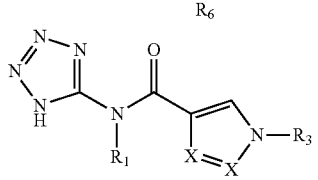
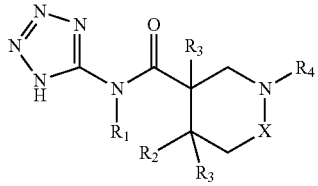
-continued
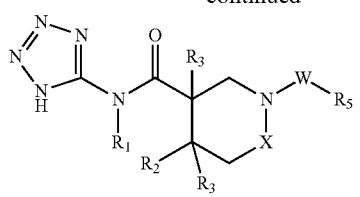
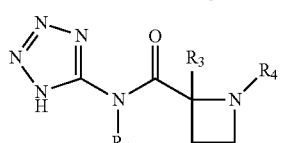
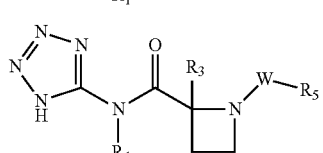
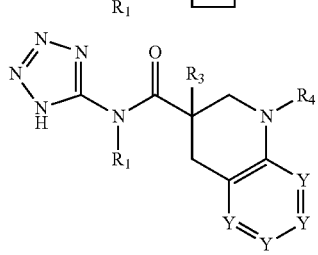
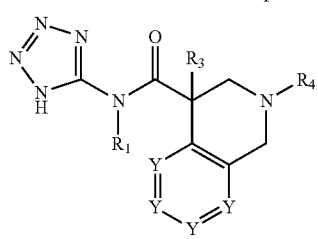
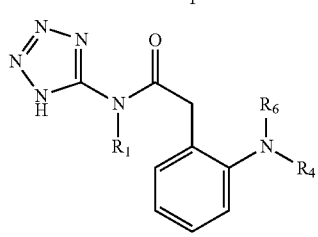
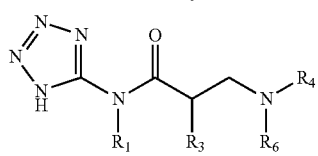
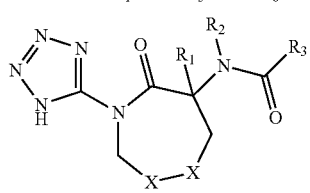
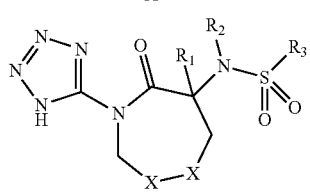

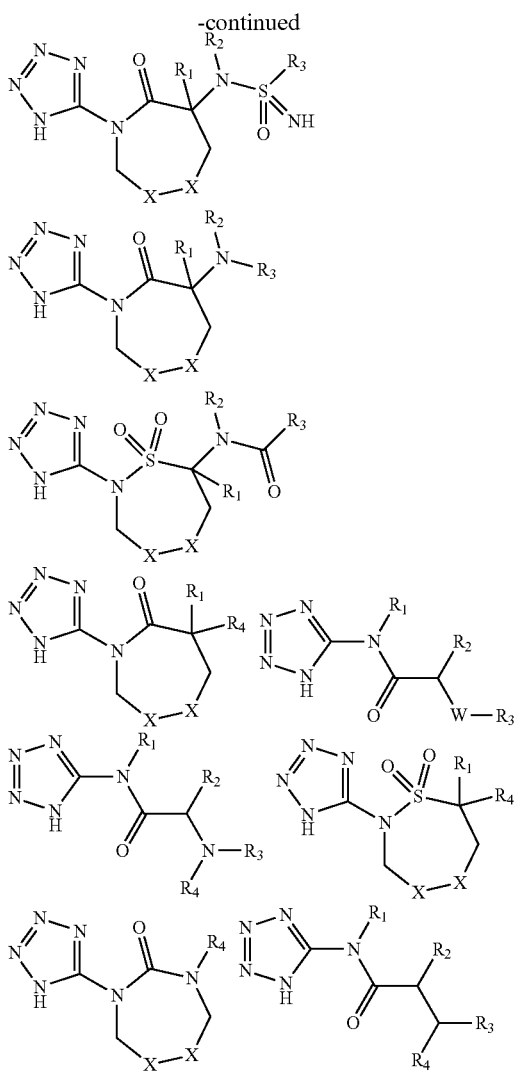

wherein each W is independently selected from: O, NO, S, SO, $CH_2$, $NMe_2$, CHMe, $C(Me)_2$, $CF_2$, or $SO_2$; wherein each X and Y are independently selected from: O, NH, NO, NMe, $NMe_2$, S, SO, $SO_2$, $CF_2$, C(=O), CH, N, $CR_2$, $(CH_2)_n$, where n=1 or 2, a "bond", or $CMe_2$ or in the alternative X—Y together are selected from: CH=CH, cyclopropyl, or $(CH_2)_n$, where n=1 or 2; wherein each R1 is independently selected from: H, a halogen, an optionally substituted alkyl group, optionally substituted aryl or heteroaryl group; wherein each R2 is independently selected from: H, a halogen $CH_3$, an optionally substituted alkyl group, or optionally substituted aryl or heteroaryl group, OMe, $NH_2$, $N(Me)_2$, or an amine having alkyl group side chains; wherein each R3 is independently selected from: H, a halogen, optionally substituted aryl or heteroaryl group, an optionally substituted alkyl group; wherein each R4 is independently selected from: H, a halogen, optionally substituted aryl or heteroaryl group, an optionally substituted alkyl group, acylated substituted and unsubstituted aryl or heteroaryl systems, including amides and sulfonamides; wherein each R5 is independently selected from: H, a halogen, optionally substituted aryl or heteroaryl group, an optionally substituted alkyl group; and wherein each R6 is independently selected from: H, a halogen, an optionally substituted alkyl group.

An embodiment of the present disclosure includes a pharmaceutical composition that includes a therapeutically effective amount of a beta-lactamase inhibitor (e.g., such as those described above and herein), or a pharmaceutically acceptable salt of the beta-lactamase inhibitor, and a pharmaceutically acceptable carrier, to treat a condition.

An embodiment of the present disclosure includes a method of treating a condition that includes: delivering to a subject in need thereof, a pharmaceutical composition, wherein the pharmaceutical composition includes a therapeutically effective amount of a beta-lactamase inhibitor (e.g., such as those described above and herein), or a pharmaceutically acceptable salt of the beta-lactamase inhibitor, and a pharmaceutically acceptable carrier, to treat the condition, wherein the beta-lactamase inhibitor has one of the following structures Other structures, compositions, methods, features, and advantages will be, or become, apparent to one with skill in the art upon examination of the following drawings and detailed description. It is intended that all such additional structures, compositions, methods, features, and advantages be included within this description, be within the scope of the present disclosure, and be protected by the accompanying claims.

DISCUSSION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of organic chemistry, biochemistry, molecular biology, pharmacology, medicine, and the like, which are within the skill of the art. Such techniques are explained fully in the literature.

Prior to describing the various embodiments, the following definitions are provided and should be used unless otherwise indicated.

Definitions

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "substituted" refers to any one or more hydrogens on the designated atom that can be replaced with a selection from the indicated group, provided that the designated atom's normal valence is not exceeded, and that the substitution results in a stable compound. For example, when a substituent is keto (i.e., C—C(═O)—C), then 2 hydrogens on the atom can be replaced. Keto substituents are not present on aromatic moieties. When a ring system (e.g., carbocyclic or heterocyclic) is substituted with a double bond, it is intended that the carbonyl group or double bond be part of the ring.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as halogen, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below. In an embodiment, "substituted" includes the substituted group may contain in place of one or more hydrogens a group such as halogen or an alkyl group (e.g., a linear or branched C1 to C4 moiety).

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, indazolyl, quinolyl, isoquinolyl, quinoxalyl, and quinazolinyl. Preferred examples are furanyl, indazolyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —S(O$_2$)—R, wherein R may be, but is not limited to, alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—S(O$_2$)CH$_3$) and the like.

The term "phosphite" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure into a host. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition, a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of a tumor or a disease in a host (e.g., a mammal, typically a human or non-human animal of veterinary interest), and includes: (a) reducing the risk of occurrence of the disease in a subject determined to be predisposed to the condition or disease but not yet diagnosed with it (b) impeding the development of the condition or disease, and/or (c) relieving the condition disease, e.g., causing regression of the condition or disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition, a disease, or a symptom thereof and/or may be therapeutic in terms of a partial or complete cure for a condition, a disease, and/or adverse effect attributable to the disease.

As used herein, the term "host," "subject," or "patient," includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

Discussion

The present disclosure provides compositions including a beta-lactamase inhibitor, pharmaceutical compositions including a beta-lactamase inhibitor, methods of treatment of a condition (e.g., infection) or disease, methods of treatment using compositions or pharmaceutical compositions, and the like. Embodiments of the present disclosure can be used to achieve broad-spectrum activity against both serine and metallo beta-lactamases. An embodiment of the present disclosure can be used in combination (e.g., in the same composition or separately) to treat resistant strains of bacteria (e.g., serine and metallo beta-lactamases). Additional details are described in the Examples.

The production of beta-lactamase is one of the main resistance mechanisms against beta-lactam antibiotics. Beta-lactamases are divided into four groups determined by their mechanism of action and amino acid similarity. Classes A, C, and D are serine beta-lactamases that utilize a serine residue in the active site that becomes catalytically activated as a nucleophile attacking the beta-lactam causing hydrolysis of the beta-lactam ring contained in the antibiotic. Class B beta-lactamases carry out hydrolysis of the beta-lactam ring by using zinc ion in the active site. Embodiments of the present disclosure can be used to achieve broad-spectrum activity across classes A-D (e.g., KPC-2, CTX M-14, and NDM-1 beta-lactamases) even though the mechanisms of action are very different. In this regard, embodiments of the present disclosure provides for novel beta-lactamase inhibitors that can be used alone or in combination with other beta-lactam antibiotics to treat or prophylactically treat infection. In an aspect, the beta-lactamase inhibitors and the beta-lactam antibiotic can be administered simultaneously (e.g., in the same pill or in two different pills), at different times (e.g., in two different pills), or using a time release action (e.g., the same or different pills) where the beta-lactamase inhibitors and the beta-lactam antibiotic can be released so one or both are present, where the specific way in which the beta-lactamase inhibitors and the beta-lactam antibiotic are administered are designed to achieve the desired effect.

In addition, embodiments of the present disclosure include beta-lactamase inhibitors that can be used in combination with a beta-lactam antibiotic to treat resistant strands of bacteria. In an embodiment, the beta-lactam antibiotic can include penicillin and penicillin derivatives, cephalosporin and cephalosporin derivatives, monobactam and monobactam derivatives, carbapenem and carbapenem derivatives, and a combination thereof. In an embodiment, the beta-lactam antibiotic can include benzylpenicillin, ampicillin, amoxicillin, loracarbef, cephalothin, cefotaxime, ceftazidime, cefepime, aztreonam, imipenem, meropenem, or the like. In an embodiment, the derivatives described regarding a beta-lactam antibiotic derivatives are those known in the art.

An embodiment of the present disclosure includes a composition and pharmaceutical composition including a beta-lactamase inhibitor. In an aspect, the pharmaceutical composition and the method of treatment (e.g., of an infection such as one directly or indirectly caused by a bacterial infection) includes a therapeutically effective amount of a beta-lactamase inhibitor, or a pharmaceutically acceptable salt of the beta-lactamase inhibitor, and a pharmaceutically acceptable carrier, to treat a condition (e.g., bacterial infection), which can be optionally combined with another beta-lactam antibiotic.

In an embodiment the bacterial infections can be caused by one or more types of bacteria, in particular, drug or multidrug resistant bacteria. In an aspect, the bacteria can include, but is not limited to, bacteria expressing serine beta-lactamases and metallo beta-lactamases (e.g., classes A, B, C, and D beta-lactamases) or a combination of bacteria. Specifically, the bacteria can include *Klebsiella pneumoniae, Pseudomonas aeruginosa*, Enterobacteriaceae such as *Escherichia coli, Acinetobacter baumannii, Bacillus pumilus*, other Gram-negative or -positive bacteria or a combination thereof. In an aspect, the different beta-lactamases can include Class A enzymes such as KPC-2, CTX-M-15 and SHV-2, Class B enzymes such as NDM-1, VIM-2 and IMP-1, Class C enzymes such as AmpC and CMY, and Class D enzymes such as OXA-10 and OXA-48.

In an embodiment, the composition or pharmaceutical composition includes a beta-lactamase inhibitor that can be represented by any one of the following general structures as well as pharmaceutically acceptable salts of these. For each of the compounds in Groups 1-5 as well as any other compounds described herein, if a moiety (e.g., R1-R6, W, X, Y, or the like) is used more than once in a compound, each use of the moiety is independently selected (e.g., for example, if Y is used in 4 places, each instance of Y is independently selected (e.g., one Y can be CH, another Y can be N, another Y can be CR2, or and another Y can be NO) and each can be different, the same or the like).

Group 1 structures:

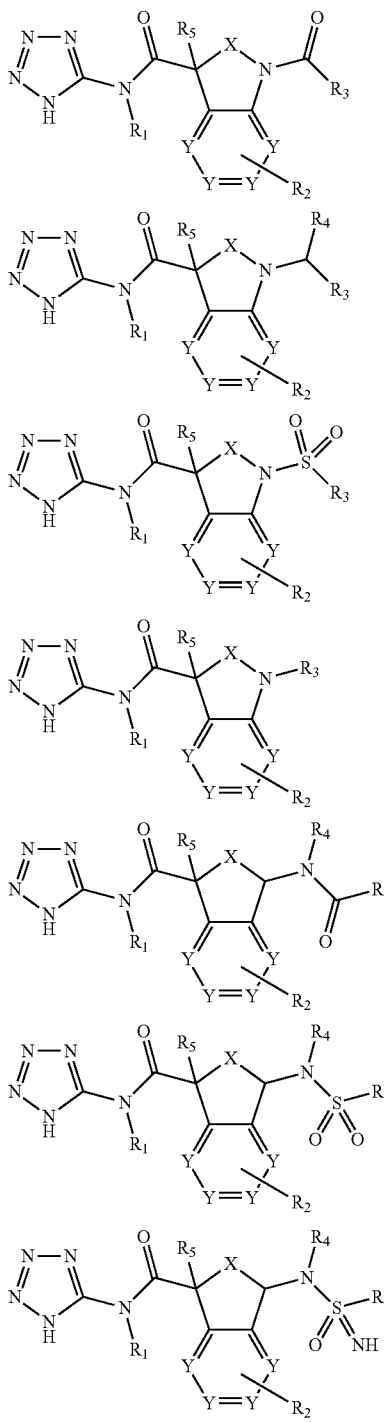

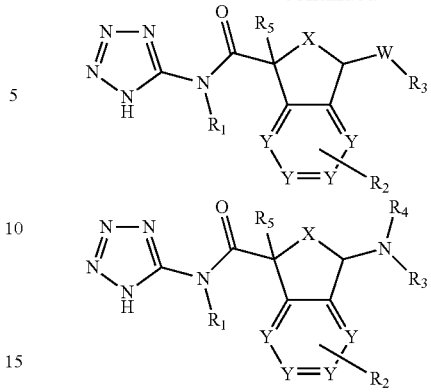

In regard to group 1, W can be selected from: O, NO, S, SO, or $SO_2$.

In regard to group 1, X can be selected from: O, NH, NO, NMe, S, SO, $SO_2$, C(=O), $CF_2$, $CMe_2$, or $(CH_2)_n$, where n=1 or 2.

In regard to group 1, Y can be selected from: CH, N, $CR_2$, or NO.

In regard to group 1, R1 can be selected from H, a halogen, or an optionally substituted alkyl group (e.g., a C1 to C6 linear or branched alkyl groups such as Me, iPr, tBu, optionally substituted with a halogen such as F).

In regard to group 1, R2 can be selected from: H, a halogen (e.g., F), $CH_3$, OMe, $NH_2$, $N(Me)_2$, or an amine having alkyl group side chains (e.g., the side chains can be C1 to C6 linear or branch alkyl group).

In regard to group 1, R3 can be selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 1, R4 can be selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 1, R5 can be selected from: H, a halogen (e.g., F), optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

Group 2 structures:

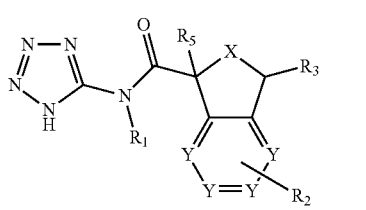

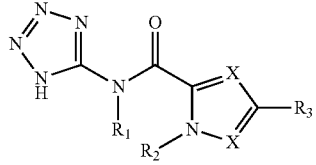

-continued

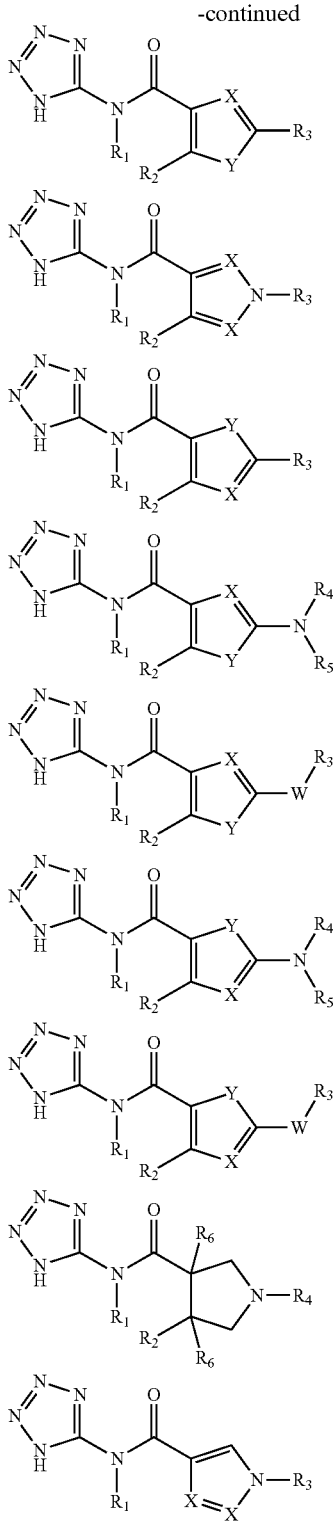

In regard to group 2, W can be selected from: $CH_2$, O, S, SO, $SO_2$, NO, or $NMe_2$.

In regard to group 2, X can be selected from: CH or N.

In regard to group 2, Y can be selected from: O, S, SO, $SO_2$, NH, NO, or NMe.

In regard to group 2, R1 can be selected from: H, a halogen, or an optionally substituted alkyl group (e.g., a C1 to C6 linear or branched alkyl groups such as Me, iPr, tBu, optionally substituted with a halogen such as F).

In regard to group 2, R2 can be selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 2, R3 can be selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 2, R4 can be selected from: H, a halogen, optionally substituted aryl or heteroaryl group (e.g., a thiophene group, an imidazole group, a benzimidazole group, a pyrmidone group), an optionally substituted alkyl group (e.g., a C1 to C6 linear or branched alkyl groups such as Me, iPr, tBu, optionally substituted with a halogen such as F), or acylated substituted and unsubstituted aryl or heteroaryl systems, including amides and sulfonamides.

In regard to group 2, R5 is selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 2, R6 is selected from: H, a halogen, or an optionally substituted alkyl group (e.g., a C1 to C6 linear or branched alkyl groups such as Me, iPr, tBu, optionally substituted with a halogen such as F).

Group 3 structures:

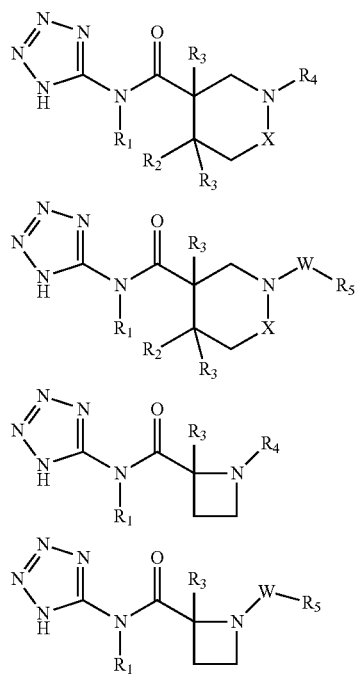

-continued

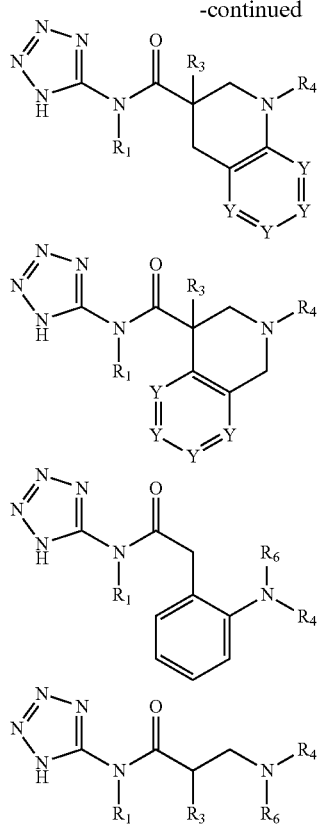

In regard to group 3, W is selected from: CH$_2$, CHMe, C(Me)2, or CF$_2$.

In regard to group 3, X is a "bond" or (CH$_2$)$_n$, where n=1 or 2.

In regard to group 3, Y is selected from CH, N, or NO.

In regard to group 3, R1 is selected from: H, a halogen, or an optionally substituted alkyl group (e.g., a C1 to C6 linear or branched alkyl groups such as Me, iPr, tBu, optionally substituted with a halogen such as F).

In regard to group 3, R2 is selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 3, R3 is selected from: H, a halogen (e.g., F), or an optionally substituted alkyl group (e.g., a C1 to C6 linear or branched alkyl groups such as Me, iPr, tBu, optionally substituted with a halogen such as F).

In regard to group 3, R4 is selected from: H, a halogen, optionally substituted aryl or heteroaryl group (e.g., a thiophene group, an imidazole group, a benzimidazole group, a pyrmidone group), an optionally substituted alkyl group (e.g., a C1 to C6 linear or branched alkyl groups such as Me, iPr, tBu, optionally substituted with a halogen such as F), or acylated substituted and unsubstituted aryl or heteroaryl systems, including amides and sulfonamides.

In regard to group 3, R5 is selected from: H, a halogen, optionally substituted aryl or heteroaryl group (e.g., a thiophene group, an imidazole group, a benzimidazole group, a pyrmidone group), or an optionally substituted alkyl group (e.g., a C1 to C6 linear or branched alkyl groups such as Me, iPr, tBu, optionally substituted with a halogen such as F).

In regard to group 3, R6 is selected from: H, a halogen, or an optionally substituted alkyl group (e.g., a C1 to C6 linear or branched alkyl groups such as Me, iPr, tBu, optionally substituted with a halogen such as F).

Group 4 structures:

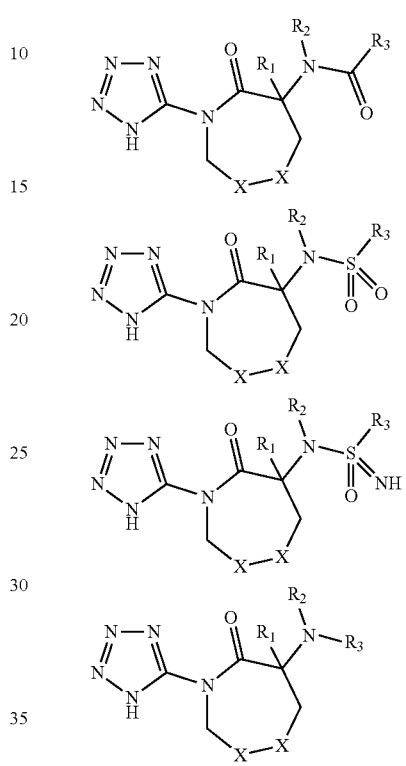

In regard to group 4, X and Y can be independently selected from: O, NH, NO, NMe, NMe$_2$, S, SO, SO$_2$, CF$_2$, CH$_2$, or CMe$_2$. In the alternative, X—Y together can be selected from: CH═CH, cyclopropyl, or (CH$_2$)$_n$, where n=1 or 2.

In regard to group 4, R1 can be selected from: H, a halogen (e.g., F), an optionally substituted alkyl group (e.g., a C1 to C6 linear or branched alkyl groups such as Me, iPr, tBu, optionally substituted with a halogen such as F), or optionally substituted aryl or heteroaryl group (e.g., a thiophene group, an imidazole group, a benzimidazole group, a pyrmidone group).

In regard to group 4, R2 can be selected from: H, a halogen (e.g., F), an optionally substituted alkyl group (e.g., a C1 to C6 linear or branched alkyl groups such as Me, iPr, tBu, optionally substituted with a halogen such as F), or optionally substituted aryl or heteroaryl group (e.g., a thiophene group, an imidazole group, a benzimidazole group, a pyrmidone group).

In regard to group 4, R3 can be selected from: H, a halogen (e.g., F), an optionally substituted alkyl group (e.g., a C1 to C6 linear or branched alkyl groups such as Me, iPr, tBu, optionally substituted with a halogen such as F), or optionally substituted aryl or heteroaryl group (e.g., a thiophene group, an imidazole group, a benzimidazole group, a pyrmidone group).

Group 5 structures:

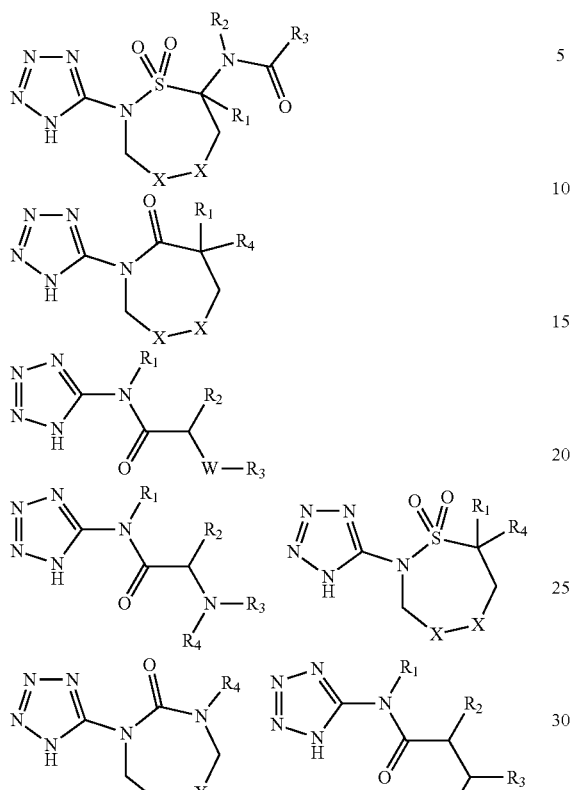

In regard to group 5, W can be selected from: O, NO, S, SO, or SO$_2$.

In regard to group 5, R1 can be selected from: H, a halogen (e.g., F), or an optionally substituted alkyl group (e.g., a C1 to C6 linear or branched alkyl groups such as Me, iPr, tBu, optionally substituted with a halogen such as F).

In regard to group 5, R2 can be selected from: H, a halogen (e.g., F), an optionally substituted alkyl group (e.g., a C1 to C6 linear or branched alkyl groups such as Me, iPr, tBu, optionally substituted with a halogen such as F), or optionally substituted aryl or heteroaryl group (e.g., a thiophene group, an imidazole group, a benzimidazole group, a pyrmidone group).

In regard to group 5, R3 can be selected from: H, a halogen (e.g., F), an optionally substituted alkyl group (e.g., a C1 to C6 linear or branched alkyl groups such as Me, iPr, tBu, optionally substituted with a halogen such as F), or optionally substituted aryl or heteroaryl group (e.g., a thiophene group, an imidazole group, a benzimidazole group, a pyrmidone group).

In regard to group 5, R4 can be selected from: H, a halogen (e.g., F), an optionally substituted alkyl group (e.g., a C1 to C6 linear or branched alkyl groups such as Me, iPr, tBu, optionally substituted with a halogen such as F), or optionally substituted aryl or heteroaryl group (e.g., a thiophene group, an imidazole group, a benzimidazole group, a pyrmidone group).

Illustrative examples of making compounds from each of groups 1-5 are provided in Example 1. These examples provide a basis for making the other compounds in groups 1-5.

In an embodiment, the composition or pharmaceutical composition includes a beta-lactamase inhibitor that can be represented by any one of the following compounds as well as pharmaceutically acceptable salts of these, where each of these compounds can be substituted.

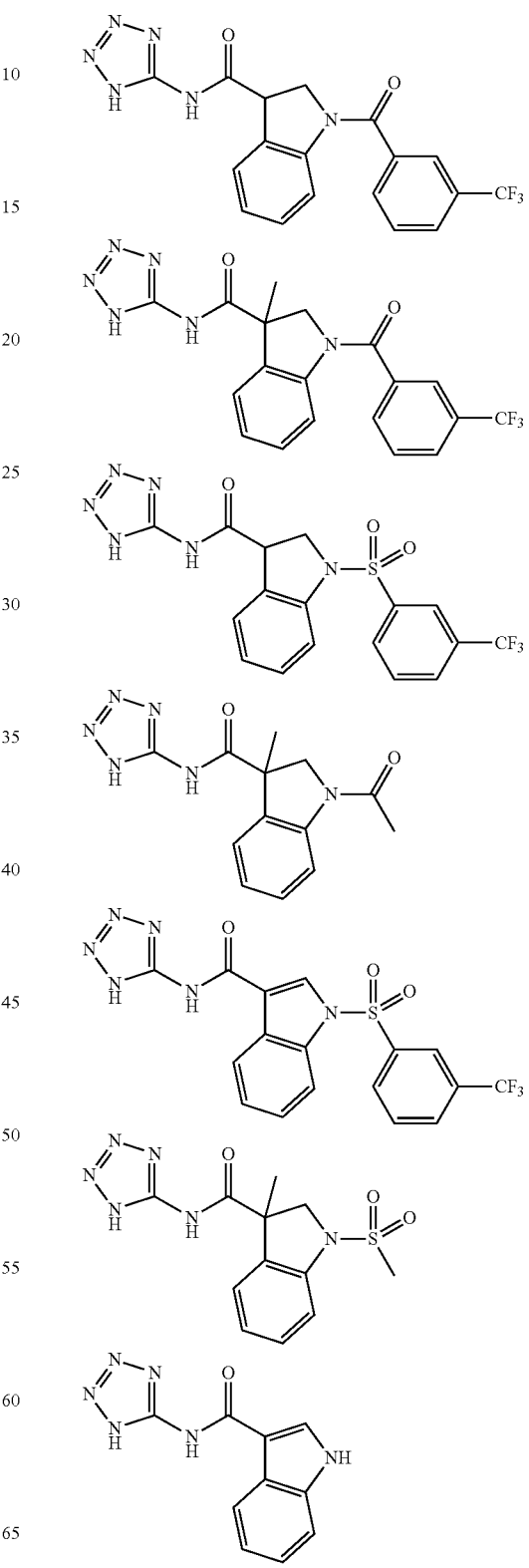

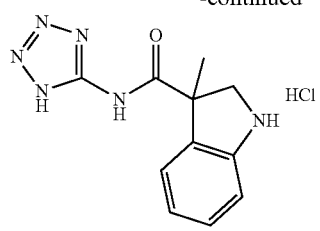
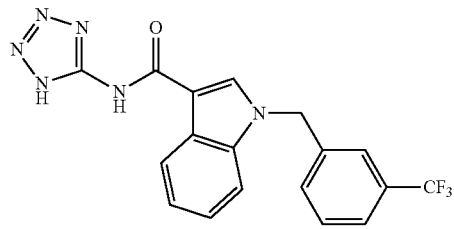
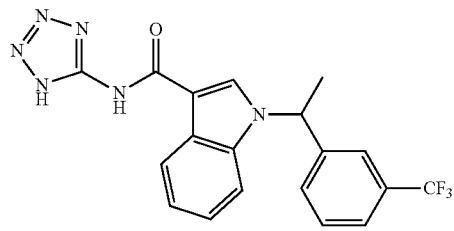
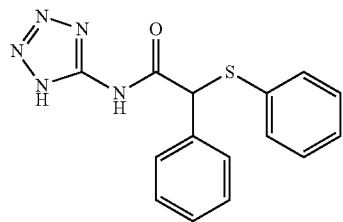
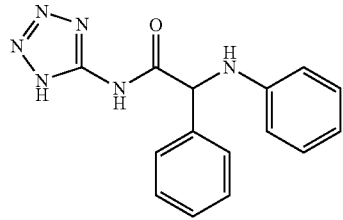
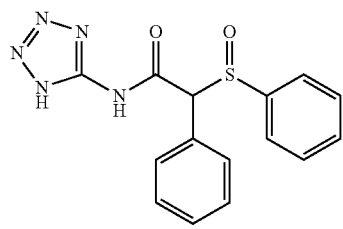
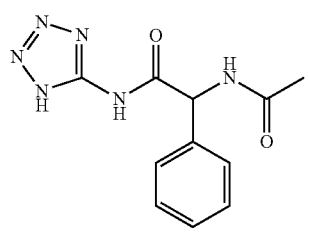
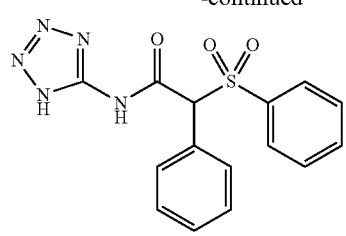
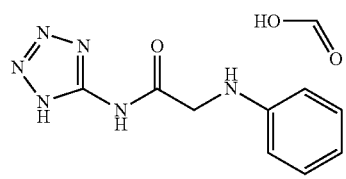
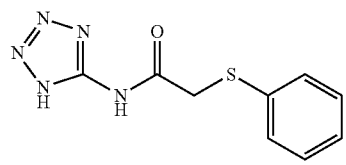
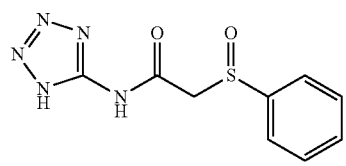
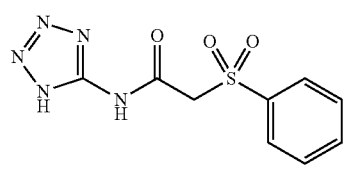
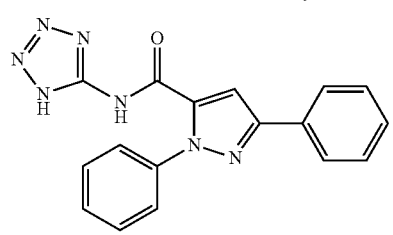
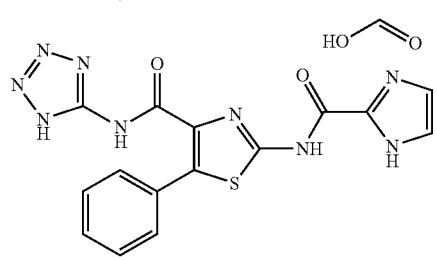
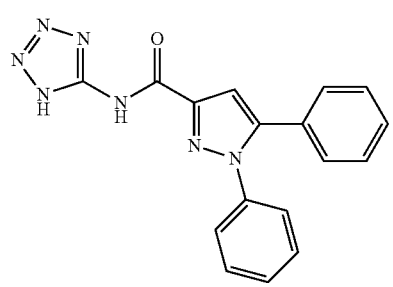

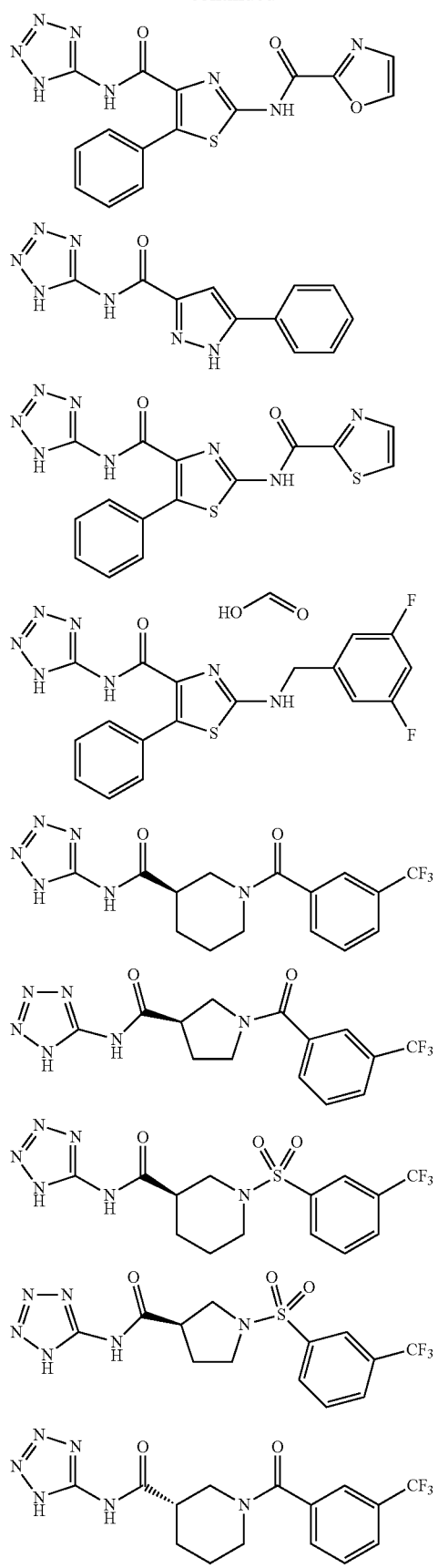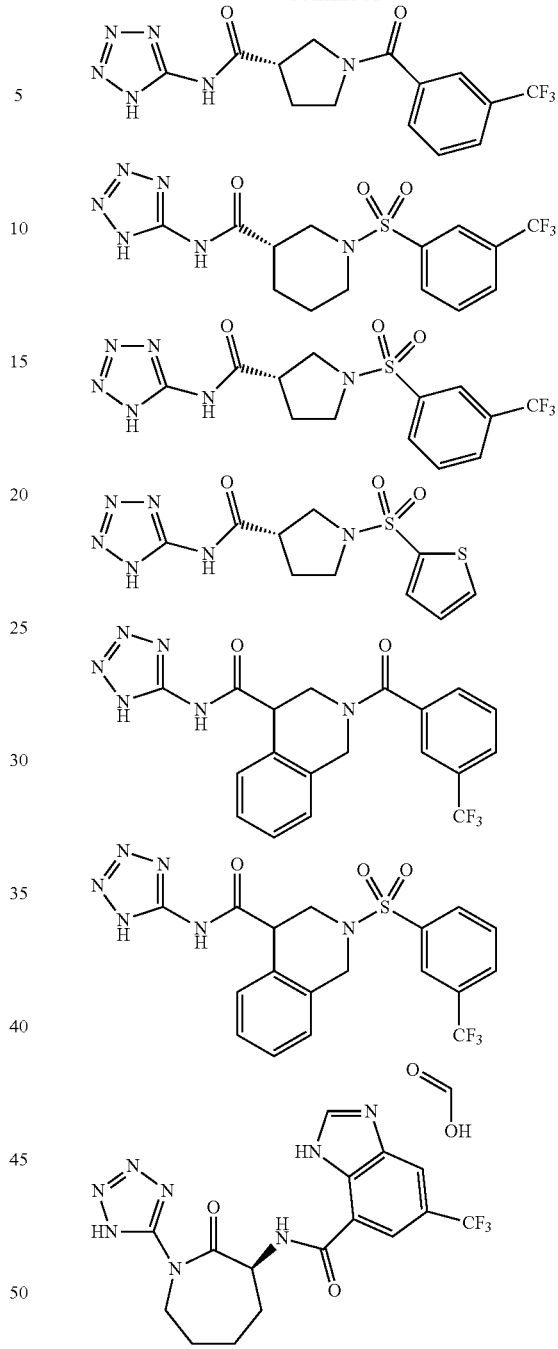

It should be noted that the therapeutically effective amount to result in uptake of the beta-lactamase inhibitor and/or antibiotic (e.g., each either alone or in combination with one another) into the subject will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Pharmaceutical Formulations and Routes of Administration

Embodiments of the present disclosure include a beta-lactamase inhibitor as identified herein and can be formulated with one or more pharmaceutically acceptable excipients, diluents, carriers and/or adjuvants. In addition, embodiments of the present disclosure include a beta-lactamase inhibitor formulated with one or more pharmaceutically acceptable auxiliary substances. In particular beta-lactamase inhibitor can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the beta-lactamase inhibitor can be administered to the host using any means capable of resulting in the desired effect. Thus, the beta-lactamase inhibitor can be incorporated into a variety of formulations for therapeutic administration. For example, the beta-lactamase inhibitor can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the beta-lactamase inhibitor may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the beta-lactamase inhibitor can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the beta-lactamase inhibitor can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the beta-lactamase inhibitor can be utilized in aerosol formulation to be administered via inhalation. Embodiments of the beta-lactamase inhibitor can be formulated into pressurized acceptable propellants such as dichlorodifluoromethane, propane, nitrogen and the like.

Furthermore, embodiments of the beta-lactamase inhibitor can be made into suppositories by mixing with a variety of bases such as emulsifying bases or water-soluble bases. Embodiments of the beta-lactamase inhibitor can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the beta-lactamase inhibitor in a composition as a solution in sterile water, normal saline or another pharmaceutically acceptable carrier.

Embodiments of the beta-lactamase inhibitor can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the beta-lactamase inhibitor can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the beta-lactamase inhibitor can be accomplished using any of a variety of refillable, pump systems. Pumps provide consistent, controlled release over time. In some embodiments, the beta-lactamase inhibitor can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the beta-lactamase inhibitor) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the beta-lactamase inhibitor are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the beta-lactamase inhibitor adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the beta-lactamase inhibitor may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the beta-lactamase inhibitor described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the beta-lactamase inhibitor can be administered to a host in one or more doses. Those of skill will readily appreciate that dose levels can vary as a function of the specific the beta-lactamase inhibitor administered, the severity of the symptoms and the susceptibility of the subject to side effects. Preferred dosages for a given compound are readily determinable by those of skill in the art by a variety of means.

In an embodiment, multiple doses of the beta-lactamase inhibitor are administered. The frequency of administration of the beta-lactamase inhibitor can vary depending on any of a variety of factors, e.g., severity of the symptoms, and the like. For example, in an embodiment, the beta-lactamase inhibitor can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the beta-lactamase inhibitor is administered continuously.

The duration of administration of the beta-lactamase inhibitor analogue, e.g., the period of time over which the beta-lactamase inhibitor is administered, can vary, depending on any of a variety of factors, e.g., patient response, etc. For example, the beta-lactamase inhibitor in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the beta-lactamase inhibitor) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the beta-lactamase inhibitor) can be administered in a single dose or in multiple doses.

Embodiments of the beta-lactamase inhibitor can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the beta-lactamase inhibitor. Where systemic delivery is desired, administration typically involves invasive or systemically absorbed topical or mucosal administration of pharmaceutical preparations.

In an embodiment, the beta-lactamase inhibitor can also be delivered to the subject by enteral administration. Enteral routes of administration include, but are not limited to, oral and rectal (e.g., using a suppository) delivery.

Methods of administration of the beta-lactamase inhibitor through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Methods

Expression and Purification of Beta-Lactamases—

For His tag KPC-2 beta-lactamase, bacteria were grown overnight at 30 C with shaking in 50 mL LB broth supplemented with 50 µg/mL kanamycin. Two liters of LB broth supplemented with 50 µg/mL kanamycin, 200 mM sorbitol, and 5 mM betaine were each inoculated with 10 mL of overnight bacterial culture. Cultures were then grown at 37 C until an optical density at 600 nm ($OD_{600}$) of 0.6-0.7. Protein expression was then initiated by the addition of IPTG (final concentration 0.5 mM), followed by growth for 16 hr at 20 C. Cells were pelleted by centrifugation and stored at −80 C until further use. The his tag KPC-2 beta-lactamase was purified by nickel affinity chromatography and gel filtration. Briefly, the cell pellets were thawed and re-suspended in 40 mL of buffer A (20 mM Tris-HCl pH 8.0, 300 mM NaCl, 20 mM imidazole) with one complete protease inhibitor cocktail tablet (Roche) and disrupted by sonication, followed by ultracentrifugation to clarify the lysate. After ultracentrifugation, the supernatant was passed through a 0.22 µm filter before loading onto a 5 mL HisTrap HP affinity column (GE Healthcare Life Sciences, USA) pre-equilibrated with buffer A. His tag KPC-2 was eluted by a linear imidazole gradient (20 mM to 500 mM). Fractions were analyzed by SDS-PAGE. Fractions containing his tag KPC-2 were concentrated using a 10 k NMWL Amicon Ultra-15 Centrifugal Filter Unit. Concentrated his tag KPC-2 was then loaded onto a superdex 75 gel filtration column (GE Healthcare Life Sciences) pre-equilibrated with 20 mM Tris-HCl pH 8.0, 300 mM NaCl. Protein concentration was determined by absorbance at 280 using an extinction coefficient of 39,545. SDS-PAGE analysis indicated that the eluted protein was more than 95% pure.

For sumo tag NDM-1 metallo-beta-lactamase, bacteria were grown overnight at 30 C with shaking in 50 mL LB broth supplemented with 100 µg/mL ampicillin. Two liters of LB broth supplemented with 100 µg/mL ampicillin were each inoculated with 10 mL of overnight bacterial culture. Cultures were then grown at 37 C until an optical density at 600 nm ($OD_{600}$) of 0.6-0.7. Protein expression was then initiated by the addition of IPTG (final concentration 0.5 mM), followed by growth for 16 hr at 20 C. Cells were pelleted by centrifugation and stored at −80 C until further use. The sumo tag NDM-1 beta-lactamase was purified by nickel affinity chromatography and gel filtration. Briefly, the cell pellets were thawed and re-suspended in 40 mL of buffer A (20 mM HEPES pH 7.4, 0.5 M NaCl, 20 mM imidazole) with one complete protease inhibitor cocktail tablet (Roche) and disrupted by sonication, followed by ultracentrifugation to clarify the lysate. After ultracentrifugation, the supernatant was passed through a 0.22 µm filter before loading onto a 5 mL HisTrap HP affinity column (GE Healthcare Life Sciences, USA) pre-equilibrated with buffer A. Sumo tag NDM-1 was eluted by a linear imidazole gradient (20 mM to 500 mM). Fractions were analyzed by SDS-PAGE. Fractions containing sumo tag NDM-1 were buffer exchanged into 20 mM HEPES pH 7.0, 100 mM NaCl. Cleavage of the sumo tag was then carried out with ULP1 protease overnight at room temperature and then concentrated using a 10 k NMWL Amicon Ultra-15 Centrifugal Filter Unit. The sample was then loaded back onto a nickel affinity column and the flow through was collected, containing the untagged NDM-1. NDM-1 was concentrated and loaded onto a gel filtration column (GE Healthcare Life Sciences) pre-equilibrated with 20 mM HEPES pH 7.0, 100 mM NaCl. Protein concentration was determined by absorbance at 280 using an extinction coefficient of 27,960. SDS-PAGE analysis indicated that the eluted protein was more than 95% pure.

Steady-State Kinetic Analysis—

Steady-state kinetic parameters were determined by using a Biotek Cytation 5 Cell Imaging Multi-Mode Reader. For KPC-2 and CTX M-14, each assay was performed in 100 mM Tris-HCl pH 7.0, 0.01% Triton X-100 at 37 C. $V_{max}$ and $K_m$ were determined from initial steady-state velocities from nitrocefin read at a wavelength of 486 nm. The kinetic parameters were obtained using the non-linear portion of the data to the Henri-Michaelis (equation 1) using Gera version 2.07.

$$V=V\max[S]/(K_m+[S]) \quad \text{(Equation 1)}$$

$IC_{50}$, defined as the inhibitor concentration that results in a 50% reduction of nitrocefin (20 µM for KPC-2 and 50 µM for CTX M-14) hydrolysis was determined by measurements of initial velocities after mixing 1 nM of KPC-2 or CTX M-14 with increasing concentrations of inhibitors. The inhibition constant ($K_i$) was calculated according to equation 2:

$$K_i=IC_{50}/([S]/K_m+1) \quad \text{(Equation 2)}$$

For NDM-1, the procedures were the same as above except the assay was performed in 100 mM Tris-HCl pH 7.0, 1 µM ZnSO4, 0.01% Triton X-100. In addition, a nitrocefin concentration of 10 µM was used.

MIC Studies

Compounds were tested for synergy with the carbapenem antibiotic, imipenem, against BL21(DE3) E. coli expressing KPC-2. MIC values were determined with the Mueller-Hinton broth microdilution method. To test for inhibitory activity, compounds were dissolved in DMSO and dilutions were carried out using LB broth. Compounds were test at 100 µM with increasing concentrations of imipenem. A control was performed with DMSO to demonstrate that DMSO did not have an effect on bacteria growth. After inoculation, the plates are incubated at 37 C for 24 hours. The MIC of the compounds are then determined visually. MIC data are shown in Table 1.

TABLE 1

MICs of imipenem when combined with select tetrazole-based derivatives.

| | MIC (µg/mL) | |
|---|---|---|
| Strain | Imipenem | Imipenem + NT-69 |
| E. coli BL21(DE3) pET-GST-bla$_{KPC-2}$ | 2 | 1 |

Crystallization and Soaking Experiments

Crystallization trials were carried out by using Qiagen crystallization kits. An initial condition for KPC-2 was found in the Classics suite A4 containing 2 M Ammonium sulfate and 5% (v/v) isopropanol. Crystals of his tag KPC-2 were grown at 20 C using the hanging-drop vapor diffusion in EasyXtal 15-Well tools (Qiagen). Protein solutions (10-20 mg/ml) in 20 mM Tris-HCl pH 8.0, 300 mM NaCl were mixed 1:2 (v/v) with a reservoir solution containing 2 M ammonium sulfate and either 5% (v/v) isopropanol or 5% (v/v) ethanol. Droplets (1.5 µL) were micro seeded with 0.5 µL of diluted seed stock. Crystals typically began to form within two weeks. To obtain the inhibitor bound structures, KPC-2 crystals were soaked in a solution containing 1.44 M sodium citrate and 10 mM of tetrazole-based derivatives for 1 hour. The soaked crystals were cryo-protected in a solution containing 1.15 M sodium citrate, 20% (v/v) glycerol, and 0.5 mM tetrazole-based derivative and cryo-cooled in liquid nitrogen.

The CTX M-14 crystallization buffer was previously optimized with a condition of 1.6 M sodium potassium phosphate buffer pH 8.3 at 20 C. A protein solution of 25.6 mg/mL was mixed 2:2 with the reservoir solution. Droplets of 4 µL were microseeded with 0.5 µL of diluted seed stock. Crystals typically began to form within 3-4 days. To obtain the inhibitor bound structures CTX M-14 crystals were soaked in a solution containing the reservoir solution and 10-20 mM of tetrazole-based derivatives for 4-12 hours. The soaked crystals were cryo-protected in a solution containing 8.3 sodium potassium phosphate, 30% (v/v) sucrose, and 0.5 mM tetrazole-based derivatives and cryo-cooled in liquid nitrogen.

NDM-1 was crystallized using conditions of 0.2 M calcium acetate and 20% (w/v) PEG3350. Protein solution of 60 mg/mL was mixed 1 µL of protein to 2 µL of reservoir solution. Crystals formed anywhere between 2-24 hours. To obtain the inhibitor bound structures NDM-1 crystals were soaked in a solution containing the reservoir solution and 10-20 mM of tetrazole based derivatives for 1-4 hours. The soaked crystals were cryo-protected in a solution containing 0.2 M calcium acetate and 20% (w/v) PEG3350, 30% (v/v) glycerol, and 0.5 mM tetrazole based derivatives and cryo-cooled in liquid nitrogen.

Data Collection and Structure Determinations

Data for the CTX M-14, KPC-2, NDM-1 complex structures were collected at the Advanced Photon Source (APS) beamline 22-ID-D and at the Advanced Light Source (ALS) beamline 8.3.1. Diffraction data were indexed and integrated with HKL2000 and scaled with SCALA from the CCP4 suite. Phasing was performed using molecular replacement with the program Molrep from the CCP4 suite with the truncated KPC-2 structure (PDB 3C5A). Structure refinement was performed using refmac5 from the CCP4 suite and model building in WinCoot. The program Sketcher in CCP4 was used to obtain geometry restraint information for the tetrazole-based derivatives.

Materials

General Procedure A.

A dry vial or flask is charged with carboxylic acid (1 equiv) and dry N,N-dimethylformamide (1-4 mL). N,N'-diisopropylethylamine (2.1-4 equiv) is then added, followed by O-(7-azabenzotriazol-1-yl)-N,N,N',N'-tetramethyluronium hexafluorophosphate (1-1.1 equiv). After stirring for 10 minutes, partner amine (1.1-1.5 equiv) is added, and the reaction mixture is stirred at room temperature for 24 h or until judged complete by LC/MS analysis. The mixture is purified by reverse phase HPLC (Waters)(Bridge C18, MeOH:Water, 0.05% formic acid) to afford the desired product.

General Procedure B.

A dry vial or flask is charged with carboxylic acid (1 equiv) and dry N,N-dimethylformamide (1-2 mL). N,N'-diisopropylethylamine (4 equiv) is then added, followed by O-(7-azabenzotriazol-1-yl)-N,N,N',N'-tetramethyluronium hexafluorophosphate (1.1 equiv). After stirring for 10 minutes, partner amine (1.5 equiv) is added, followed by 4-dimethylaminopyridine (0.5 equiv). The reaction mixture is stirred at room temperature for 24 h or until judged complete by LC/MS analysis. The mixture is purified by reverse phase HPLC (Waters XBridge C18, MeOH:Water, 0.05% formic acid) to afford the desired product.

General Procedure C.

A dry vial or flask is charged with carboxylic acid (1 equiv), dry N,N-dimethylformamide (1-2.5 mL), and partner amine (1-1.2 equiv). N,N'-diisopropylethylamine (2-2.2 equiv) is then added, followed by O-(7-azabenzotriazol-1-yl)-N,N,N',N'-tetramethyluronium hexafluorophosphate (1.1 equiv). The reaction mixture is stirred at room temperature for 24 h or until judged complete by LC/MS analysis. The mixture is purified by reverse phase HPLC (Waters)(Bridge C18, MeOH:Water, 0.05% formic acid) to afford the desired product.

General Procedure D.

A dry vial or flask is charged with amine or relevant salt thereof (1.1 equiv) and suspended or dissolved in N,N-dimethylformamide (1.5-2 mL). The reaction mixture is cooled to 0° C. with an ice bath, upon which N,N'-diisopropylethylamine (2.1-5 equiv) is then added dropwise, and allowed to stir for 5 minutes. Desired acid chloride or sulfonyl chloride (1 equiv) is then added dropwise at 0° C.; the reaction mixture is allowed to slowly warm to room temperature overnight. The crude reaction mixture is then transferred to a seperatory funnel using dichloromethane, and rinsed three times with brine. The organic layer is dried over $MgSO_4$, rotovaped, and purified on a silica column with relevant concentrations of ethyl acetate:hexanes to afford the desired product.

General Procedure E.

A vial or flask is charged with methyl ester (1 equiv) and 4 mL of methanol. The reaction mixture is cooled to 0° C. with an ice bath, upon which 4 mL aqueous 1M LiOH is then added dropwise; the reaction mixture is allowed to slowly warm to room temperature overnight. The resultant suspension is then rotovaped to remove the methanol, and transferred to a seperatory funnel using ethyl acetate and brine. The aqueous layer is adjusted to pH 1 using 3.2M HCl, and extracted three times with ethyl acetate. The combined organic layers are dried over $MgSO_4$ and rotovaped to dryness to afford the desired product.

The illustrative procedures for making the Group 1-5 structures can be modified to produce other compounds provided in each group.

Illustrative Procedure for Group 1 Structures:

N-(1H-tetrazol-5-yl)-1-(3-(trifluoromethyl)benzoyl)indoline-3-carboxamide (2)

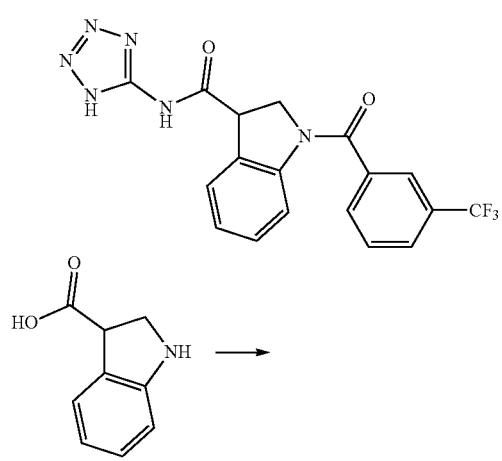

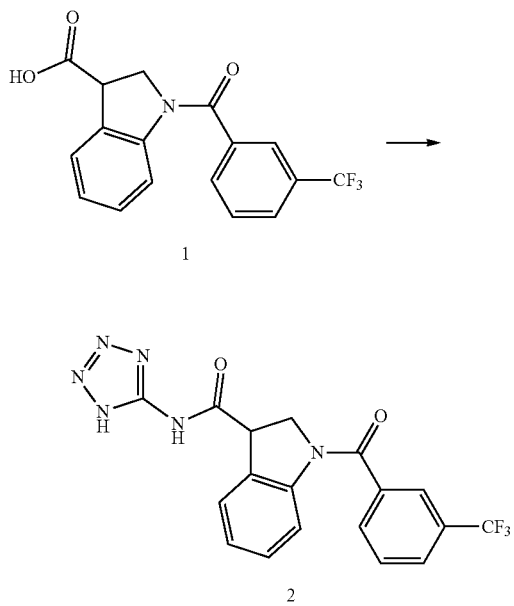

1-(3-(trifluoromethyl)benzoyl)indoline-3-carboxylic acid (1)

Commercially available indoline-3-carboxylic acid was reacted with commercially available 3-(trifluoromethyl)benzoic acid according to general procedure A to afford the title compound in 13% yield; LCMS (ESI) m/z 336 (M+H), 334 (M−H).

N-(1H-tetrazol-5-yl)-1-(3-(trifluoromethyl)benzoyl)indoline-3-carboxamide (2)

1-(3-(trifluoromethyl)benzoyl)indoline-3-carboxylic acid (2) was reacted with commercially available 5-Aminotetrazole monohydrate according to general procedure B to afford the title compound in 17% yield; LCMS (ESI) m/z 403 (M+H), 401 (M−H).

Illustrative Procedures for Group 2 Structures:

1,5-diphenyl-N-(1H-tetrazol-5-yl)-1H-pyrazole-3-carboxamide (3)

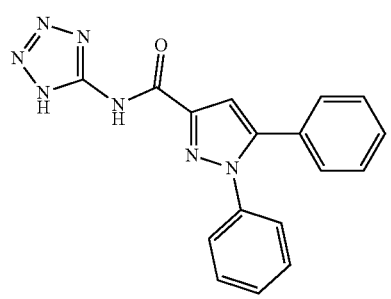

-continued

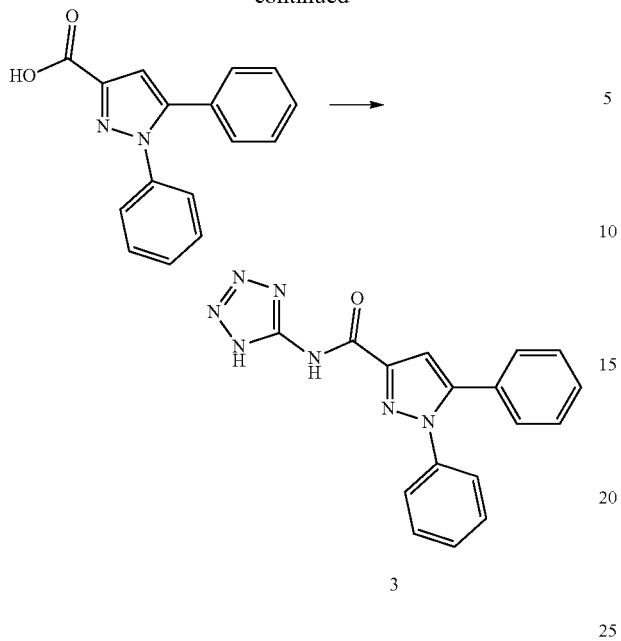

3

1,5-diphenyl-N-(1H-tetrazol-5-yl)-1H-pyrazole-3-carboxamide (3)

Commercially available 1,5-diphenyl-1H-pyrazole-3-carboxylic acid was reacted with commercially available 5-aminotetrazole monohydrate according to general procedure C to afford the title compound in 24% yield; LCMS (ESI) m/z 332 (M+H), 330 (M−H).

N-(4-((1H-tetrazol-5-yl)carbamoyl)-5-phenylthiazol-2-yl)thiazole-2-carboxamide (6)

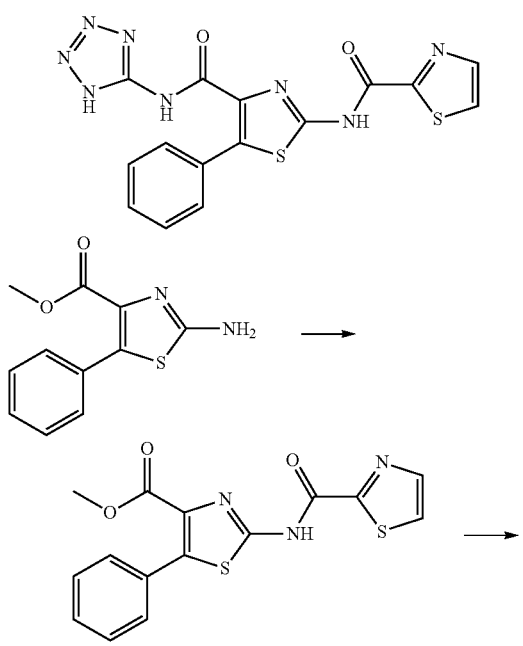

-continued

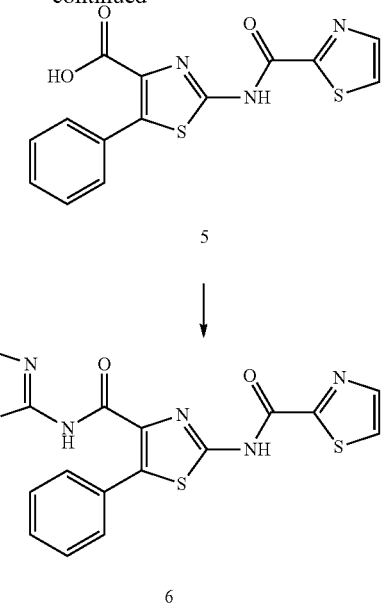

6 methyl 5-phenyl-2-(thiazole-2-carboxamido)thiazole-4-carboxylate (4)

Commercially available thiazole-2-carboxylic acid was reacted with commercially available methyl 2-amino-5-phenylthiazole-4-carboxylate according to general procedure A, with a modification to purification. In lieu of HPLC, the crude reaction mixture was transferred to a seperatory funnel with ethyl acetate and brine, and extracted thrice with ethyl acetate. The organics were combined, dried over MgSO₄, concentrated, and purified via silica column with ethyl acetate:hexanes. The relevant fractions were combined and rotovaped to afford the title compound in 40% yield; LCMS (ESI) m/z 346 (M+H).

5-phenyl-2-(thiazole-2-carboxamido)thiazole-4-carboxylic acid (5)

methyl 5-phenyl-2-(thiazole-2-carboxamido)thiazole-4-carboxylate (4) (65.2 mg, 0.2 mmol) was suspended with 4 mL methanol in a 20 mL vial. Aqueous 1M LiOH (4 mL) was then added drop wise at room temperature; the resultant suspension was allowed to stir at 45° C. for 2 h. The suspension was then rotovaped to a slurry to remove the methanol, and transferred to a seperatory funnel with 20 mL ethyl acetate and 40 mL brine. The aqueous layer was adjusted to pH 1 using 1M HCl, then extracted with 3×30 mL ethyl acetate. The organics were combined, dried over MgSO₄, and rotovaped to afford 61.2 mg of the title compound in 98% yield; LCMS (ESI) m/z 332 (M+H), 330 (M−H).

N-(4-((1H-tetrazol-5-yl)carbamoyl)-5-phenylthiazol-2-yl)thiazole-2-carboxamide (6)

5-phenyl-2-(thiazole-2-carboxamido)thiazole-4-carboxylic acid (5) was reacted with commercially available 5-aminotetrazole monohydrate according to general procedure B to afford the title compound in 44% yield; LCMS (ESI) m/z 399 (M+H), 397 (M−H).

Illustrative Procedures for Group 3 Structures:

(R)—N-(1H-tetrazol-5-yl)-1-((3-(trifluoromethyl)phenyl)sulfonyl)piperidine-3-carboxamide (9)

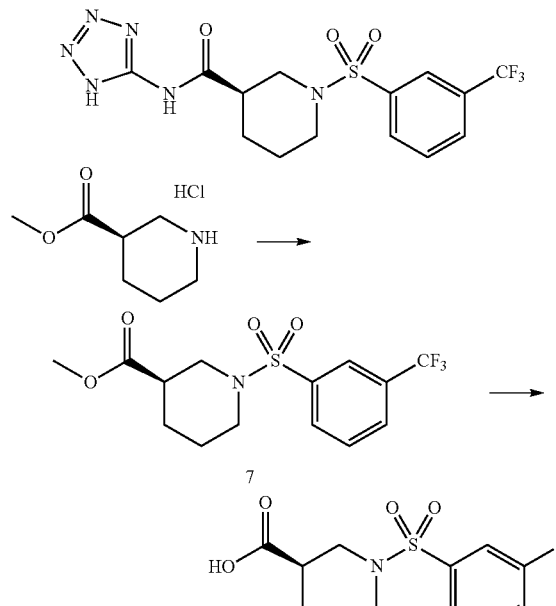

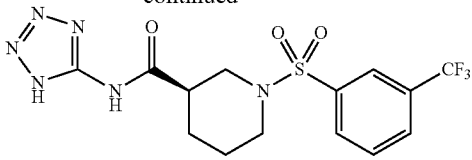

methyl (R)-1-((3-(trifluoromethyl)phenyl)sulfonyl)piperidine-3-carboxylate (7)

Commercially available methyl (R)-piperidine-3-carboxylate hydrochloride was reacted with commercially available 3-(trifluoromethyl)benzenesulfonyl chloride according to general procedure D to afford the title compound in 26% yield; LCMS (ESI) m/z 352 (M+H).

(R)-1-((3-(trifluoromethyl)phenyl)sulfonyl)piperidine-3-carboxylic acid (8)

Methyl (R)-1-((3-(trifluoromethyl)phenyl)sulfonyl)piperidine-3-carboxylate (7) was hydrolyzed according to general procedure E to afford the title compound in 99% yield; LCMS (ESI) m/z 338 (M+H), 336 (M−H).

(R)—N-(1H-tetrazol-5-yl)-1-((3-(trifluoromethyl)phenyl)sulfonyl)piperidine-3-carboxamide (9)

(R)-1-((3-(trifluoromethyl)phenyl)sulfonyl)piperidine-3-carboxylic acid (8) was reacted with commercially available 5-aminotetrazole monohydrate according to general procedure A to afford the title compound in 56% yield; LCMS (ESI) m/z 405 (M+H), 403 (M−H).

N-(1H-tetrazol-5-yl)-2-((3-(trifluoromethyl)phenyl)sulfonyl)-1,2,3,4-tetrahydroisoquinoline-4-carboxamide (13)

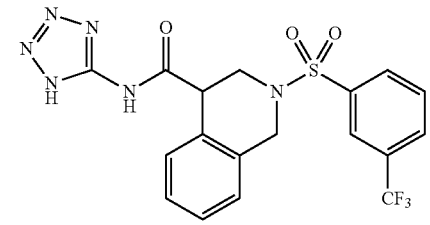

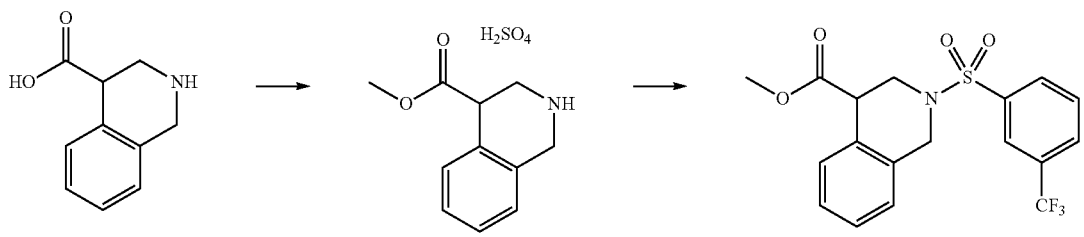

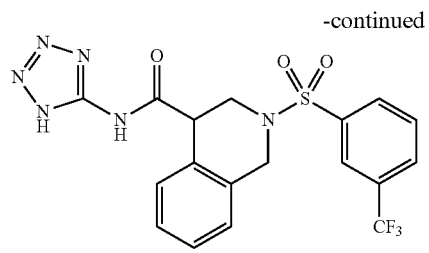

13

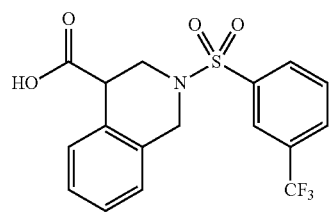

12 methyl 1,2,3,4-tetrahydroisoquinoline-4-carboxylate sulfate (10)

Commercially available 1,2,3,4-tetrahydroisoquinoline-4-carboxylic acid (100 mg, 0.6 mmol) was dissolved with 25 mL dry methanol in a 50 mL RB fitted with reflux condenser. Drops of sulfuric acid (fuming, ~30 uL) were then added, and the reaction mixture was refluxed at 95° C. for 18 h. The reaction was subsequently cooled, rotovaped to dryness, and dried for 2 days under hivac to afford the semi-crude title compound as a sulfuric acid salt in 120% yield (leftover sulfuric acid); LCMS (ESI) m/z 192 (M+H), 190 (M−H).

methyl 2-((3-(trifluoromethyl)phenyl)sulfonyl)-1,2,3,4-tetrahydroisoquinoline-4-carboxylate (11)

Methyl 1,2,3,4-tetrahydroisoquinoline-4-carboxylate sulfate (10) was reacted with commercially available 3-(trifluoromethyl)benzenesulfonyl chloride according to general procedure D to afford the title compound in 75% yield; LCMS (ESI) m/z 400 (M+H).

2-((3-(trifluoromethyl)phenyl)sulfonyl)-1,2,3,4-tetrahydroisoquinoline-4-carboxylic acid (12)

Methyl 2-((3-(trifluoromethyl)phenyl)sulfonyl)-1,2,3,4-tetrahydroisoquinoline-4-carboxylate (11) was hydrolyzed according to general procedure E, except the reaction mixture remained at room temperature the entire time. Title compound obtained in 96% yield; LCMS (ESI) m/z 386 (M+H), 384 (M−H).

N-(1H-tetrazol-5-yl)-2-((3-(trifluoromethyl)phenyl)sulfonyl)-1,2,3,4-tetrahydroisoquinoline-4-carboxamide (13)

2-((3-(trifluoromethyl)phenyl)sulfonyl)-1,2,3,4-tetrahydroisoquinoline-4-carboxylic acid (12) was reacted with commercially available 5-aminotetrazole monohydrate according to general procedure A to afford the title compound in 42% yield; LCMS (ESI) m/z 453 (M+H), 451 (M−H).

Illustrative Procedure for Group 4 Structures:

(S)—N-(2-oxo-1-(1H-tetrazol-5-yl)azepan-3-yl)-5-(trifluoromethyl)-1H-benzo[d]imidazole-7-carboxamide formate (21)

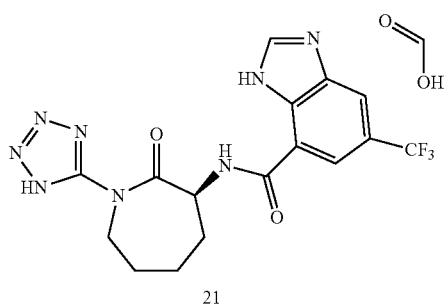

21

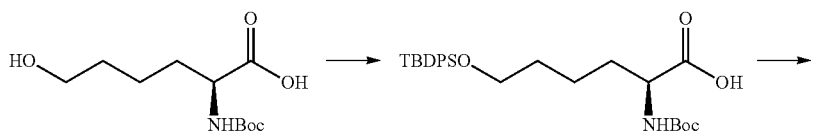

14

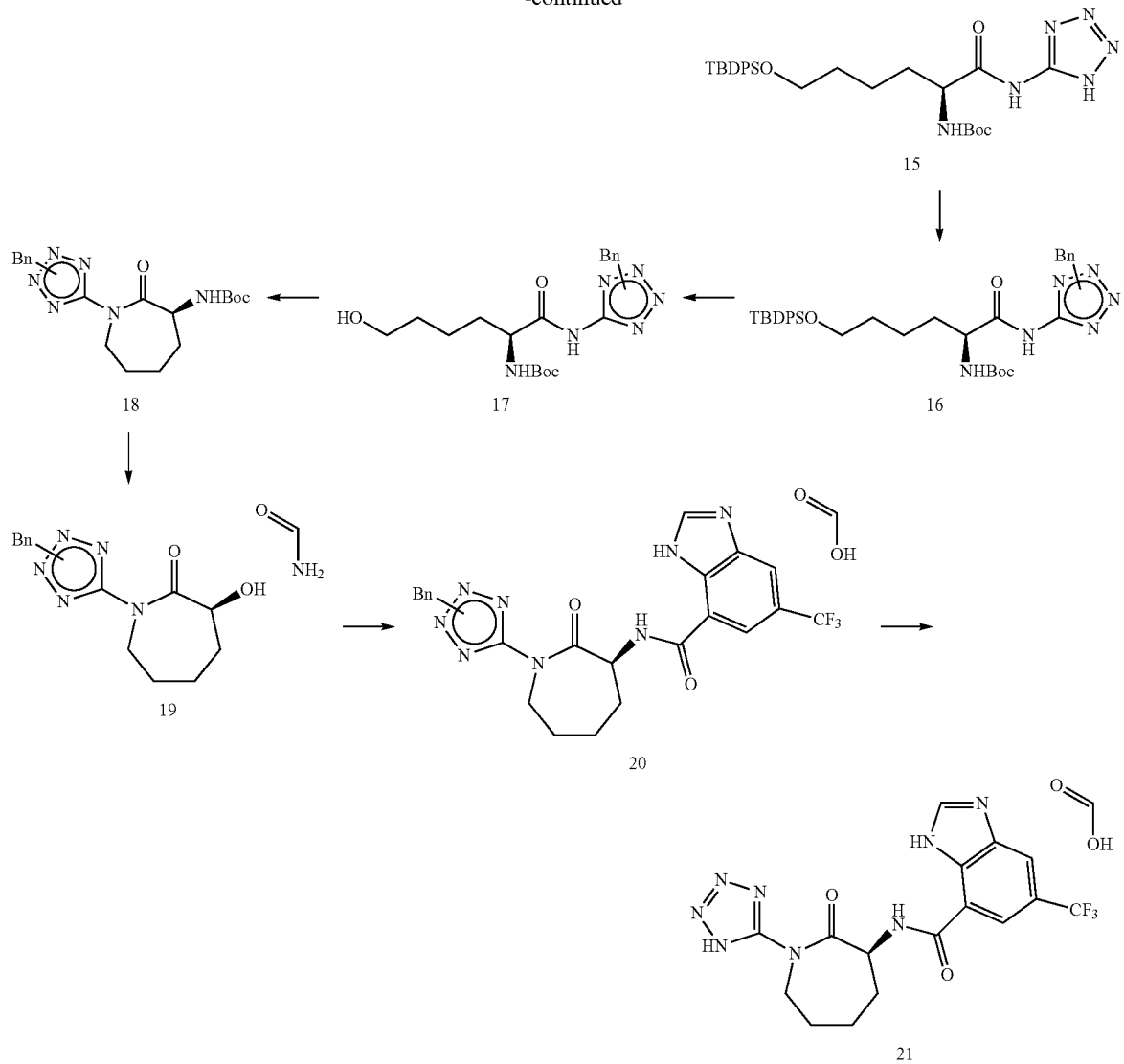

(S)-2-((tert-butoxycarbonyl)amino)-6-((tert-butyldiphenylsilyl)oxy)hexanoic acid (14)

Commercially available (S)-2-((tert-butoxycarbonyl)amino)-6-hydroxyhexanoic acid (800 mg, 3.2 mmol) was dissolved in N,N-dimethylformamide (7 mL) and cooled to 0° C. with an ice bath, tert-butyl(chloro)diphenyl silane (1.094 ml, 4.2 mmol) was then added slowly, followed by dropwise addition of pyridine (783 uL, 9.7 mmol). After stirring for 1 h at 0° C., the reaction mixture was warmed to room temperature and stirred overnight. The reaction mixture was then transferred to a seperatory funnel with 50 mL ethyl acetate and brine, and the aqueous pH adjusted to ~3 with 1M citric acid. The aqueous layer was extracted with 4×50 mL ethyl acetate; the organic layers were combined, dried over MgSO$_4$, concentrated, and purified on a silica column with 20-60% ethyl acetate:hexanes. Obtained 863.6 mg of the title compound in 55% yield; LCMS (ESI) m/z 486 (M+H), 484 (M−H).

tert-butyl (S)-(1-(((1H-tetrazol-5-yl)amino)-6-((tert-butyldiphenylsilyl)oxy)-1-oxohexan-2-yl)carbamate (15)

(S)-2-((tert-butoxycarbonyl)amino)-6-((tert-butyldiphenylsilyl)oxy)hexanoic acid (14) (600 mg, 1.2 mmol) was transferred to a 20 mL vial and dissolved with dry N,N-dimethylformamide (4 mL). N,N'-diisopropylethylamine (215 uL, 1.3 mmol) was then added, followed by O-(7-azabenzotriazol-1-yl)-N,N,N',N'-tetramethyluronium hexafluorophosphate (564 mg, 1.5 mmol). After stirring for 10 minutes, 5-aminotetrazole monohydrate (166 mg, 1.6 mmol) was added, followed by additional N,N'-diisopropylethylamine (646 uL, 3.7 mmol). The reaction mixture was stirred at room temperature for 24 h, after which it was transferred to a seperatory funnel with 50 mL ethyl acetate and brine, and the aqueous pH adjusted to ~3 with 1M citric acid. The aqueous layer was extracted with 3×50 mL ethyl acetate; the organic layers were combined, dried over MgSO$_4$, concentrated, and purified on a silica column with

(S)-tert-butyl (1-((benzyl-tetrazol-5-yl)amino)-6-((tert-butyldiphenylsilyl)oxy)-1-oxohexan-2-yl)carbamate (16)

Tert-butyl (S)-(1-((1H-tetrazol-5-yl)amino)-6-((tert-butyldiphenylsilyl)oxy)-1-oxohexan-2-yl)carbamate (15) (433 mg, 0.8 mmol) was transferred to a 20 mL vial with septa and dissolved with dry N,N-dimethylformamide (5 mL). N,N'-diisopropylethylamine (177 uL, 1 mmol) was then added, followed by 4-dimethylaminopyridine (48 mg, 0.4 mmol). After stirring for 5 minutes, benzyl bromide (112 uL, 0.9 mmol) was added dropwise, and the reaction mixture was stirred at room temperature for 18 h. The next day the reaction was quenched with 10 mL water, adjusted to pH 7 with 1M HCl, and transferred to a seperatory funnel with water and ethyl acetate. The aqueous layer was extracted with 3×30 mL ethyl acetate; the organics were combined, dried over $MgSO_4$, concentrated, and purified on a silica column with 0-50% ethyl acetate:hexanes. Obtained 100.4 mg of the title compound(s) in 20% yield (~1:1 1H vs 2H benzylation); LCMS (ESI) m/z 643 (M+H), 641 (M−H).

tert-butyl (S)-(1-((benzyl-tetrazol-5-yl)amino)-6-hydroxy-1-oxohexan-2-yl)carbamate (17)

(S)-tert-butyl (1-((benzyl-tetrazol-5-yl)amino)-6-((tert-butyldiphenylsilyl)oxy)-1-oxohexan-2-yl)carbamate (16) (100.4 mg, 0.2 mmol) was dissolved with 3 mL dry THF in a 20 mL vial with septa, and cooled to 0° C. A 1M solution of tetrabutyl ammonium fluoride in THF (783 uL, 0.8 mmol) was then added dropwise at 0° C.; the reaction mixture was subsequently warmed to room temperature and stirred overnight. The next day the reaction was quenched with 10 mL water and transferred to a seperatory funnel with 15 mL ethyl acetate and water, then extracted with 3×15 mL ethyl acetate. The combined organic layers were dried over $MgSO_4$, concentrated, and purified on a silica column with 0-50% acetone:DCM. Obtained 61.2 mg of the title compound(s) in 97% yield (~1:1 1H vs 2H benzylation); LCMS (ESI) m/z 405 (M+H), 403 (M−H).

tert-butyl (S)-(1-(benzyl-tetrazol-5-yl)-2-oxoazepan-3-yl)carbamate (18)

Tert-butyl (S)-(1-((benzyl-tetrazol-5-yl)amino)-6-hydroxy-1-oxohexan-2-yl)carbamate (17) (61.2 mg, 0.2 mmol) was put into a dried 10 mL RB and dissolved with 2 mL dry THF. Tri-n-butylphosphine (151 uL, 0.6 mmol) was then added dropwise, and allowed to stir for 5 minutes. Diisopropyl azodicarboxylate (119 uL, 0.6 mmol) was then added dropwise, and the reaction mixture was stirred at room temperature for 2 h, upon which it was heated at 60° C. for 2 h, then subsequently cooled back to room temperature and allowed to stir overnight. The next day the reaction was quenched with 10 mL water and allowed to stir for 5 minutes before transferring to a seperatory funnel with an additional 5 mL of water and ethyl acetate. The aqueous layer was extracted with 4×15 mL ethyl acetate; the combined organic layers were dried over $MgSO_4$, concentrated, and purified by reverse phase HPLC (Waters)(Bridge C18, MeOH:Water, 0.05% formic acid). Obtained 94.8 mg of the mostly-clean title compound in 162% yield—excess tri-n-butylphosphine persisted throughout the purification (~1:1 1H vs 2H benzylation); LCMS (ESI) m/z 387 (M+H), 385 (M−H).

(S)-3-amino-1-(benzyl-tetrazol-5-yl)azepan-2-one formate (19)

Semi-crude tert-butyl (S)-(1-(benzyl-tetrazol-5-yl)-2-oxoazepan-3-yl)carbamate (18) (94.8 mg) was transferred to a 20 mL vial with septa. 4 mL 4M HCl in dioxane was slowly added to vial, solubilizing most of the material, and the reaction mixture was stirred at room temperature for 2 h. The crude reaction mixture was subsequently rotovaped down to dryness. The sludge re-dissolved in DMF and purified by reverse phase HPLC (Waters)(Bridge C18, MeOH:Water, 0.05% formic acid). Obtained 19.0 mg of the title compound as a formate salt in 38% yield over two steps (~1:1 1H vs 2H benzylation); LCMS (ESI) m/z 287 (M+H), 285 (M−H).

(S)—N-(1-(benzyl-tetrazol-5-yl)-2-oxoazepan-3-yl)-6-(trifluoromethyl)-1H-benzo[d]imidazole-4-carboxamide formate (20)

Previously prepared 5-(trifluoromethyl)-1H-1,3-benzodiazole-7-carboxylic acid hydrochloride (18 mg, 0.07 mmol) (Ref. J Med Chem (55) 2163-2172, 2012) was dissolved in a 3 dram vial with N,N-dimethylformamide (1 mL). N,N'-diisopropylethylamine (24 uL, 0.13 mmol) was then added, followed by O-(7-azabenzotriazol-1-yl)-N,N,N',N'-tetramethyluronium hexafluorophosphate (28 mg, 0.07 mmol). After stirring for 10 minutes, a solution of (S)-3-amino-1-(benzyl-tetrazol-5-yl)azepan-2-one formate (19) (19.0 mg, 0.07 mmol) in 1 mL N,N-dimethylformamide was added, followed by an additional 1 mL N,N-dimethylformamide rinse of the transferred vial. Additional N,N'-diisopropylethylamine (12 uL, 0.07 mmol) was subsequently added, and the reaction mixture was stirred at room temperature for 24 h. The reaction mixture was purified by reverse phase HPLC (Waters)(Bridge C18, MeOH:Water, 0.05% formic acid). Obtained 9.7 mg of the title compound as a formate salt in 29% yield (~1:1 1H vs 2H benzylation); LCMS (ESI) m/z 499 (M+H), 497 (M−H).

(S)—N-(2-oxo-1-(1H-tetrazol-5-yl)azepan-3-yl)-5-(trifluoromethyl)-1H-benzo[d]imidazole-7-carboxamide formate (21)

(S)—N-(1-(benzyl-tetrazol-5-yl)-2-oxoazepan-3-yl)-6-(trifluoromethyl)-1H-benzo[d]imidazole-4-carboxamide formate (20) was dissolved in 100 mL methanol and subjected to hydrogenation via H-Cube (flow cell hydrogenation)—10% Pd/C, 40° C., 1 atm Hz, 1 mL/min flow rate. Reaction mixture was run in a continuous loop for 60 h, after which the methanol was removed by rotovap. The resultant residue was re-dissolved in DMF and purified by reverse phase HPLC (Waters XBridge C18, MeOH:Water, 0.05% formic acid). Obtained 6.0 mg of the title compound as a formate salt in 74% yield; LCMS (ESI) m/z 455 (M+H), 453 (M−H).

Illustrative Procedure for Group 5 Structures:

2-phenyl-2-(phenylthio)-N-(1H-tetrazol-5-yl)acetamide (22)

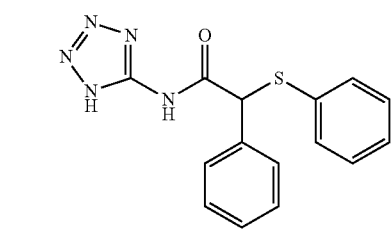

22

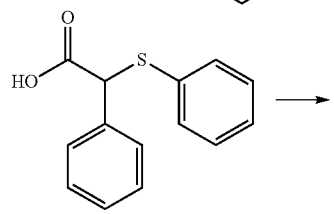

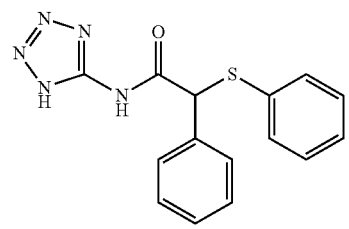

22

2-phenyl-2-(phenylthio)-N-(1H-tetrazol-5-yl)acetamide (22)

Commercially available 2-phenyl-2-(phenylthio)acetic acid was reacted with commercially available 5-aminotetrazole monohydrate according to general procedure C to afford the title compound in 22% yield; LCMS (ESI) m/z 312 (M+H), 310 (M−H).

2-phenyl-2-(phenylsulfonyl)-N-(1H-tetrazol-5-yl)acetamide (24)

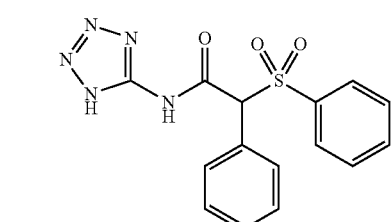

24

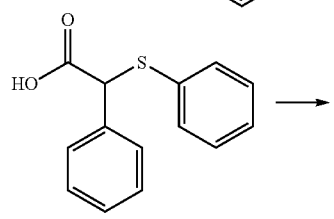

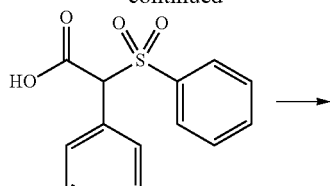

23

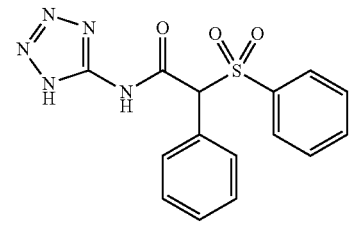

24

2-phenyl-2-(phenylsulfonyl)acetic acid (23)

Commercially available 2-phenyl-2-(phenylthio)acetic acid (150 mg, 0.6 mmol) was dissolved in 5 mL methanol in a 20 mL vial. A solution of potassium monopersulfate (867 mg, 5.2 mmol) in 4 mL water was then added drop wise at room temperature. The resultant suspension was allowed to stir at room temperature for 72 h; the suspension was then rotovaped to a slurry to remove the methanol, then suspended with 10 mL cold water. The suspension was filtered and rinsed with 3×10 mL cold water, followed by 10 mL hexanes. The white solid was dried under vacuum to afford 146.1 mg of the title compound in 86% yield; LCMS (ESI) m/z 277 (M+H), 275 (M−H).

2-phenyl-2-(phenylsulfonyl)-N-(1H-tetrazol-5-yl)acetamide (24)

2-phenyl-2-(phenylsulfonyl)acetic acid (23) (30 mg, 0.1 mmol) was suspended in a 10 mL round bottom flask with 5 mL dry DCM. 20 drops N,N-dimethylformamide were then added, followed by dropwise addition of oxalyl chloride (10 uL, 0.1 mmol). The reaction mixture was allowed to stir for 3 h at room temperature. Separately, 5-aminotetrazole monohydrate (12 mg, 0.1 mmol) was suspended in 5 mL dry DCM in a 25 mL RB flask with N,N'-diisopropylethylamine (47 uL, 0.3 mmol), and the solution was allowed to stir for 5 minutes. The aforementioned oxalyl chloride solution was then added dropwise to the suspended aminotetrazole solution, and allowed to stir at room temperature for 18 h. The combined reaction mixture was rotovaped to remove the DCM and redissolved in DMF, then purified by reverse phase HPLC (Waters)(Bridge C18, MeOH:Water, 0.05% formic acid) to afford 19.4 mg of the title compound in 52% yield; LCMS (ESI) m/z 344 (M+H), 342 (M−H).

2-phenyl-2-(phenylamino)-N-(1H-tetrazol-5-yl)acetamide (25)

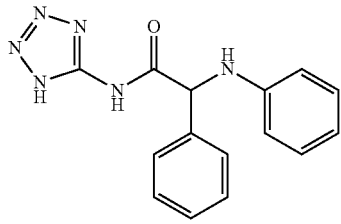

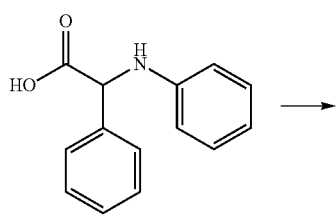

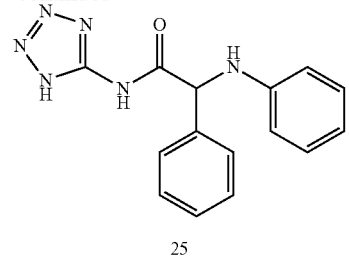

2-phenyl-2-(phenylamino)-N-(1H-tetrazol-5-yl)acetamide (25)

Commercially available anilino(phenyl)acetic acid (50 mg, 0.2 mmol) was dissolved with dry N,N-dimethylformamide (2.5 mL) in a 3 dram vial. N,N'-diisopropylethylamine (39 uL, 0.2 mmol) was then added, followed by O-(7-azabenzotriazol-1-yl)-N,N,N',N'-tetramethyluronium hexafluorophosphate (88 mg, 0.2 mmol). After stirring for 10 minutes, 5-aminotetrazole monohydrate (25 mg, 0.2 mmol) was added, followed by additional N,N'-diisopropylethylamine (43 uL, 0.2 mmol). The reaction mixture was stirred at room temperature for 24 hours. The mixture was purified by reverse phase HPLC (Waters)(Bridge C18, MeOH:Water, 0.05% formic acid) to afford the title compound in 20% yield; LCMS (ESI) m/z 295 (M+H), 293 (M−H).

Results

TABLE 2

Representative Group 1 compounds with biochemically determined $K_i$ values for diverse β-lactamases. Calculated according to the aforementioned methods section.

| Compound | Number | CTX-M14 Ki (uM) | SHV-2 Ki (uM) | KPC-2 Ki (uM) | NDM-1 Ki (uM) | OXA-48 Ki (uM) |
|---|---|---|---|---|---|---|
|  | 2 | No inhibition |  | 1.2 | 958 |  |
|  | 26 | No inhbition at 2.2 mM |  |  | No inhbition at 2.2 mM |  |
|  | 27 | No inhibition at 0.5 mM |  |  | 300 |  |

TABLE 2-continued
Representative Group 1 compounds with biochemically determined K$_i$ values for diverse β-lactamases. Calculated according to the aforementioned methods section.
| Compound | Number | CTX-M14 Ki (uM) | SHV-2 Ki (uM) | KPC-2 Ki (uM) | NDM-1 Ki (uM) | OXA-48 Ki (uM) |
|---|---|---|---|---|---|---|
| 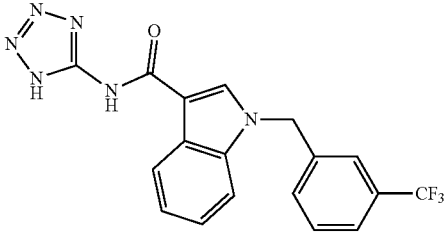 [SMILES: O=C(Nc1nnn[nH]1)c1cn(Cc2cccc(C(F)(F)F)c2)c2ccccc12] | 28 | No inhibition at 2.0 mM | No inhibition at 2.0 mM | | | |
| 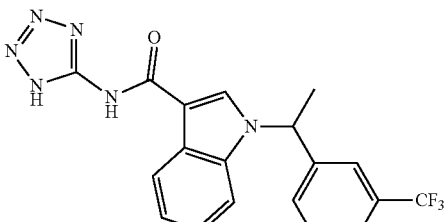 | 29 | 50% at 1900 | 50% at 1900 | | | |
| 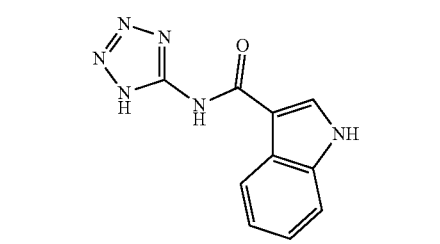 [SMILES: O=C(Nc1nnn[nH]1)c1c[nH]c2ccccc12] | 30 | | | 3000 | 354 | |
| 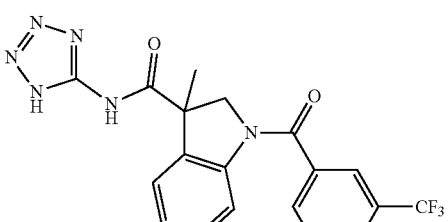 | 31 | | | 354 | 200 | |
| 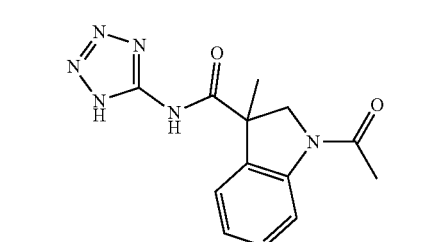 | 32 | 10% at 4800 | | 40% at 4800 | 156 | 16% at 3900 |
| 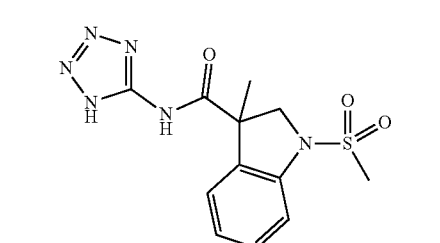 | 33 | No inhibition at 6.5 mM | | 2700 | 161 | 20% at 3900 |

TABLE 3

Representative Group 2 compounds with biochemically determined $K_i$ values for diverse β-lactamases. Calculated according to the aforementioned methods section.

| Compound | Number | CTX-M14 Ki (uM) | SHV-2 Ki (uM) | KPC-2 Ki (uM) | NDM-1 Ki (uM) | OXA-48 Ki (uM) |
|---|---|---|---|---|---|---|
| | 3 | 500 | 74% at 1000 | 11.5 | 142 | 1200 |
| | 6 | No inhibition | | 26 | No inhibition | 50% at 4800 |
| | 34 | No inhibition | | 111 | 20% at 1000 | 35% at 1600 |
| | 35 | | | | | 20% at 800 uM |
| | 36 | 2980 | | 2000 | 48 | |
| | 37 | 1000 | | 470 | 30% at 1800 | |

TABLE 3-continued

Representative Group 2 compounds with biochemically determined $K_i$ values for diverse β-lactamases. Calculated according to the aforementioned methods section.

| Compound | Number | CTX-M14 Ki (uM) | SHV-2 Ki (uM) | KPC-2 Ki (uM) | NDM-1 Ki (uM) | OXA-48 Ki (uM) |
|---|---|---|---|---|---|---|
| [structure] | 38 | 3000 | | 2000 | 40% at 3500 | |
| [structure] | 39 | 2000 | | 1500 | 10% at 1800 | |

TABLE 4

Representative Group 3, 4, and 5 compounds with biochemically determined $K_i$ values for diverse β-lactamases. Calculated according to the aforementioned methods section.

| Compound | Number | CTX-M14 Ki (uM) | SHV-2 Ki (uM) | KPC-2 Ki (uM) | NDM-1 Ki (uM) | OXA-48 Ki (uM) |
|---|---|---|---|---|---|---|
| [structure] | 9 | 243 | | 78 | No inhibition | 20% at 4800 |
| [structure] | 40 | No inhibition | | 110 | 20% at 1000 | 35% at 4800 |
| [structure] | 21 | 236 | | 60 | 30% at 1600 | No inhibition at 4.8 mM |
| [structure] | 22 | No inhbition at 2.2 mM | | 26.5 | 58 | No inhition at 1.75 mM |

TABLE 4-continued

Representative Group 3, 4, and 5 compounds with biochemically determined $K_i$ values for diverse β-lactamases. Calculated according to the aforementioned methods section.

| Compound | Number | CTX-M14 Ki (uM) | SHV-2 Ki (uM) | KPC-2 Ki (uM) | NDM-1 Ki (uM) | OXA-48 Ki (uM) |
|---|---|---|---|---|---|---|
| (structure) | 25 | No inhibition at 6.5 mM | | 519 | 652 | 40% at 5000 |
| (structure) | 41 | No inhibition at 6.5 mM | | No inhibition at 5.2 mM | No inhibition at 5.2 mM | No inhibition at 5.2 mM |
| (structure) | 42 | No inhibition at 6.5 mM | | 1200 | No inhibition at 5.2 mM | No inhibition at 5.2 mM |

DISCUSSION

The compound testing and structural analysis results have demonstrated that the tetrazole-based compounds are capable of inhibiting clinically important serine and metallo beta-lactamases by directly binding to their active sites. The tetrazole-based scaffolds described in this invention can be developed into broad-spectrum high-affinity inhibitors targeting multiple beta-lactamases in resistant bacteria, and can be combined with beta-lactam antibiotics to treat infections caused by multi-resistant bacteria.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A composition, comprising a beta-lactamase inhibitor selected from of the following structures:

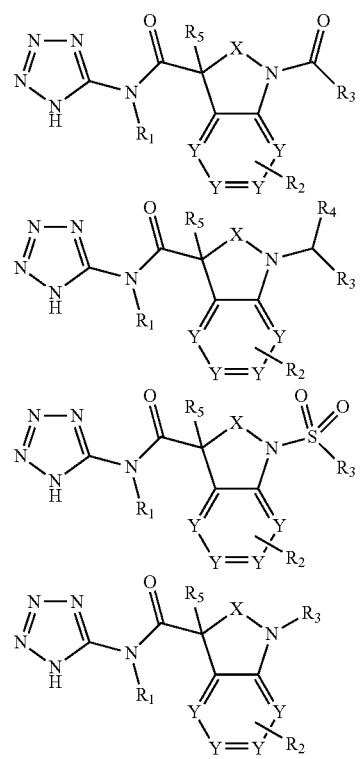

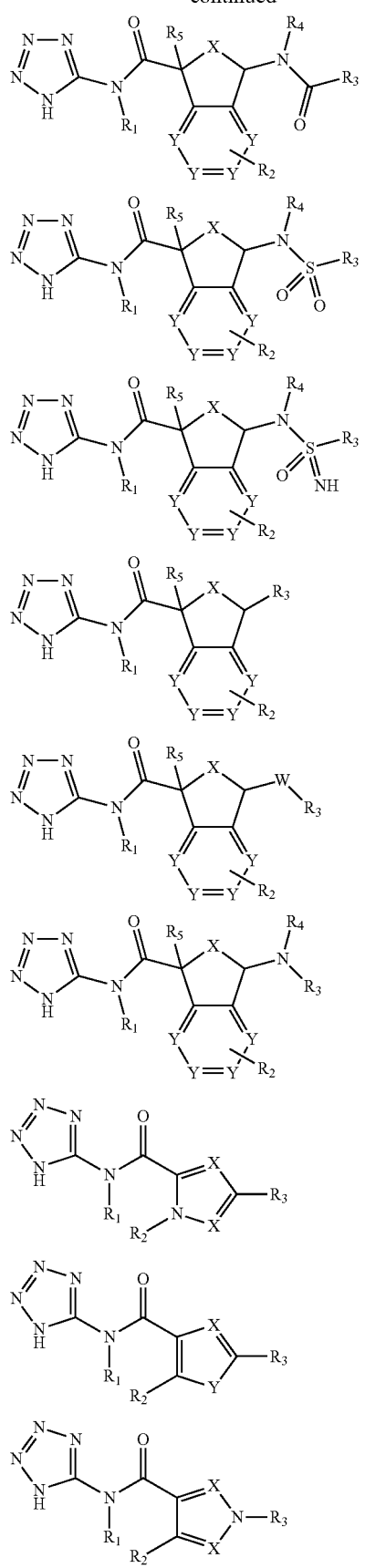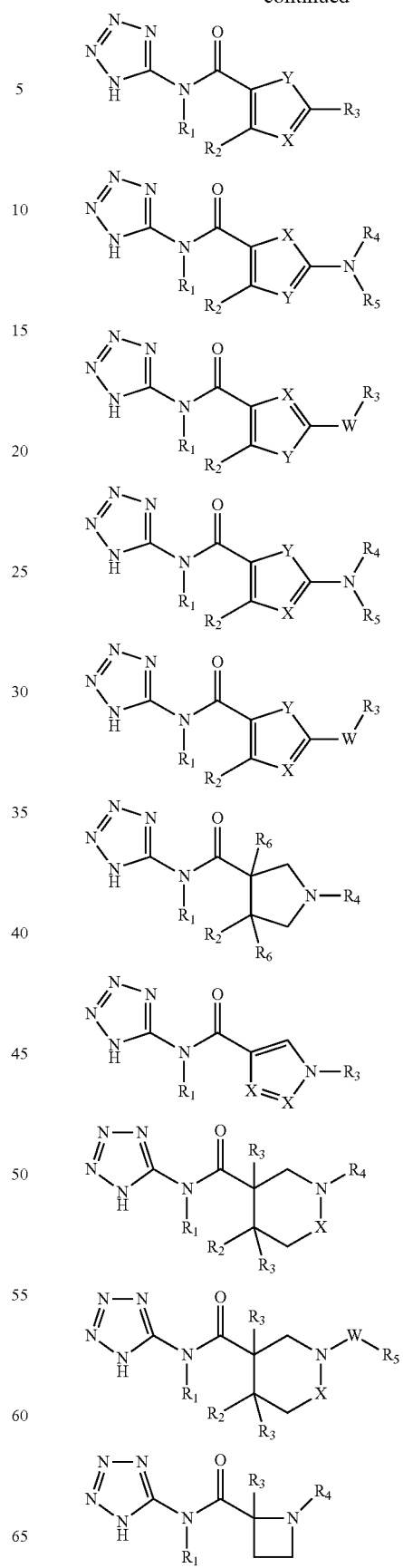

-continued

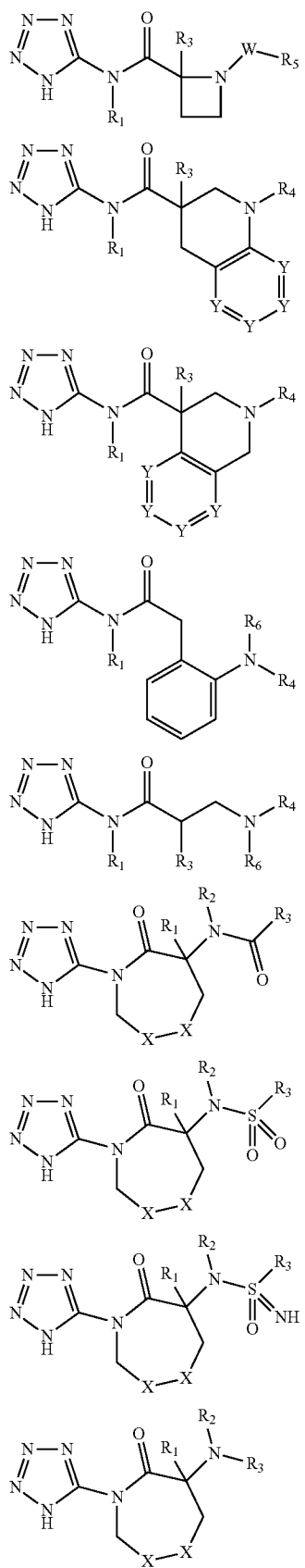

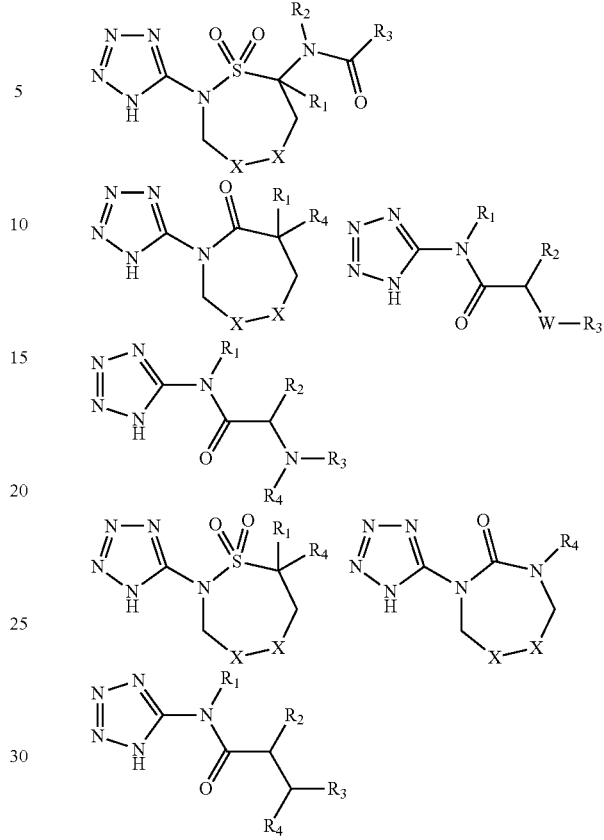

wherein each W is independently selected from: O, NO, S, SO, $CH_2$, $NMe_2$, CHMe, $C(Me)_2$, $CF_2$, or $SO_2$;

wherein X and Y are independently selected from: O, NH, NO, NMe, $NMe_2$, S, SO, $SO_2$, $CF_2$, C(=O), CH, N, CR2, $(CH_2)_n$, where n=1 or 2, a bond, or $CMe_2$ or wherein X—Y is selected from: CH=CH, cyclopropyl, or $(CH_2)_n$, where n=1 or 2;

wherein each R1 is independently selected from: H, a halogen, Me, iPr, tBu, or, optionally substituted aryl or heteroaryl;

wherein each R2 is independently selected from: H, a halogen $CH_3$, an optionally substituted alkyl, or optionally substituted aryl or heteroaryl, OMe, $NH_2$, $N(Me)_2$, or an alkyl substituted amine;

wherein each R3 is independently selected from: H, aryl, thiophene, imidazole, pyrimidone, or optionally substituted aryl or heteroaryl, Me, iPr, tBu, or; aryl, thiophene, imidazole, pyrimidone;

wherein each R4 is independently selected from: H, Me, iPr, tBu, substituted and unsubstituted aryl or heteroaryl thiophene, imidazole, pyrimidone, acylated substituted and unsubstituted aryl or heteroaryl;

wherein each R5 is independently selected from: H, F, Me, iPr, tBu, optionally substituted aryl or heteroaryl, aryl, thiophene, imidazole, pyrimidone; and wherein each R6 is independently selected from: H, Me, iPr, tBu, substituted or unsubstituted aryl or heteroaryl.

2. The composition of claim 1, further comprising an antibiotic.

3. The composition of claim 2, wherein the antibiotic is a beta-lactam antibiotic.

4. The composition of claim 1, wherein beta-lactamase inhibitor is selected from one of the following structures:

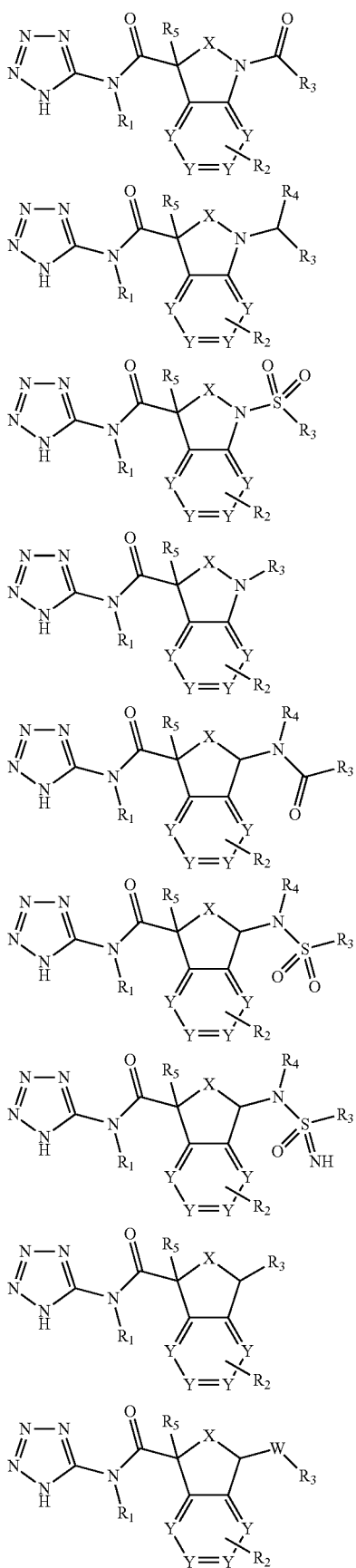

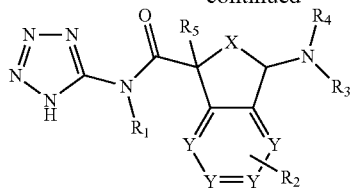

wherein each W is independently selected from: 0, NO, S, SO, or $SO_2$;

wherein each X is independently selected from: O, NH, NO, NMe, S, SO, $SO_2$, C(=O), $CF_2$, $CMe_2$, or $(CH_2)_n$, where n=1 or 2;

wherein each Y is independently selected from: CH, N, CR2, or NO;

wherein, each R1 is independently selected from H, Me, iPr, or tBu;

wherein each R2 is independently selected from: H, F, $CH_3$, OMe, $NH_2$, $N(Me)_2$, or an alkyl substituted amine;

wherein each R3 is independently selected from: H, aryl, thiophene, imidazole, benzimidazole, pyrimidone, substituted aryl or heteroaryl, Me, iPr, or tBu;

wherein each R4 is independently selected from: H, Me, iPr, tBu, or substituted and unsubstituted aryl or heteroaryl; and wherein each R5 is independently selected from: H, a halogen, F, Me, or substituted and unsubstituted aryl or heteroaryl.

5. The composition of claim 1, wherein beta-lactamase inhibitor is selected from one of the following structures:

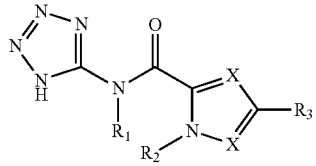

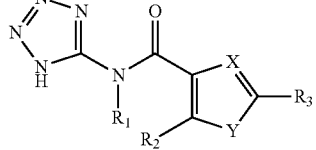

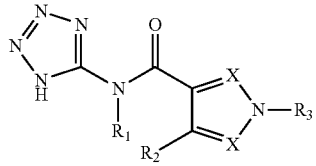

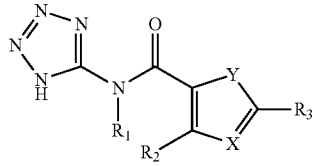

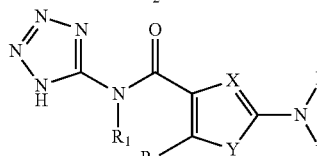

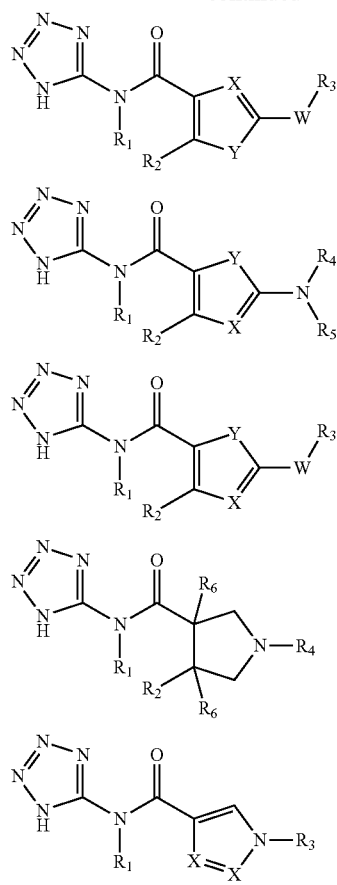

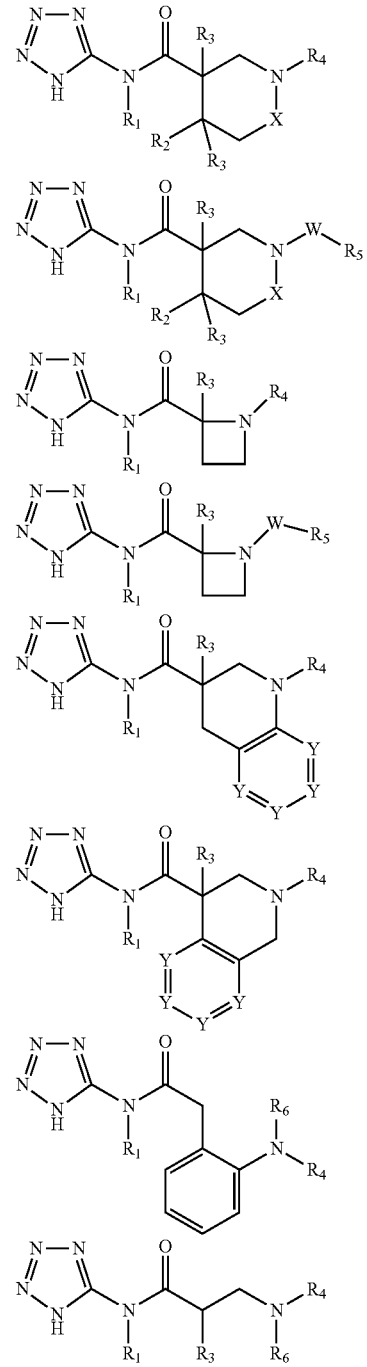

wherein each W is independently selected from: CH₂, O, S, SO, SO₂, NO, or NMe₂;

wherein each X is independently selected from: CH or N;

wherein each Y is independently selected from: O, S, SO, SO₂, NH, NO, or NMe;

wherein each R1 is independently selected from: H, Me, iPr, or tBu;

wherein each R2 is independently selected from: aryl, thiophene, imidazole, pyrimidone, substituted and unsubstituted aryl or heteroaryl; Me, iPr, tBu, or pyrimidone;

wherein each R3 is independently selected from: aryl, thiophene, imidazole, pyrimidone, heteroaryl Me, iPr, tBu, thiophene, imidazole, pyrimidone, or substituted and unsubstituted aryl or heteroaryl;

wherein each R4 is independently selected from: aryl, thiophene, imidazole, pyrimidone, substituted and unsubstituted aryl or heteroaryl Me, iPr, tBu, thiophene, imidazole, pyrimidone or substituted and unsubstituted aryl or heteroaryl;

wherein each R5 is independently selected from: H, Me, iPr, tBu, or substituted and unsubstituted aryl or heteroaryl; and wherein each R6 is independently selected from: H, F, Me, or substituted and unsubstituted aryl or heteroaryl.

6. The composition of claim 1, wherein beta-lactamase inhibitor is selected from one of the following structures:

wherein each W is independently selected from: CH₂, CHMe, C(Me)₂, or CF₂;

wherein each X is independently a "bond" or (CH₂)ₙ, where n=1 or 2;

wherein each Y is independently selected from CH, N, or NO;

wherein each R1 is independently selected from: H, Me, iPr, or tBu;

wherein each R2 is independently selected from: H, aryl, thiophene, imidazole, pyrimidone, Me, iPr, tBu, aryl, thiophene, imidazole, pyrimidone, or substituted and unsubstituted aryl or heteroaryl;

wherein each R3 is independently selected from: H, F, Me, or substituted and unsubstituted aryl or heteroaryl;

wherein each R4 is independently selected from: H, aryl, thiophene, imidazole, pyrimidone, or substituted and unsubstituted aryl or heteroaryl systems; Me, iPr, tBu, or thiophene, imidazole, pyrimidone;

wherein each R5 is independently selected from: aryl, thiophene, imidazole, pyrimidone, substituted and unsubstituted aryl or heteroaryl systems; Me, iPr, tBu, thiophene, imidazole, or pyrimidone; and wherein each R6 is independently selected from: H, Me, iPr, tBu, or substituted and unsubstituted aryl or heteroaryl.

7. The composition of claim 1, wherein beta-lactamase inhibitor is selected from one of the following structures:

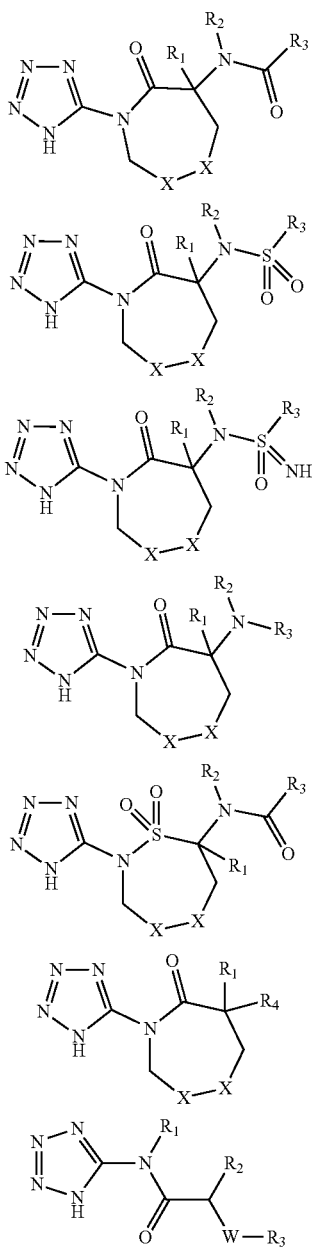

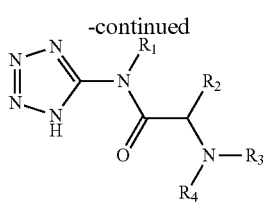

wherein X and Y are independently selected from: O, NH, NO, NMe, NMe$_2$, S, SO, SO$_2$, CF$_2$, CH$_2$, or CMe$_2$ or wherein X—Y is selected from: CH=CH, cyclopropyl, or (CH$_2$)$_n$, where n=1 or 2;

wherein each R1 is independently selected from: H, F, Me, or substituted and unsubstituted aryl or heteroaryl;

wherein each R2 is independently be selected from: H, Me, iPr, tBu, or substituted and unsubstituted aryl or heteroaryl; and wherein each R3 is independently selected from: aryl, thiophene, imidazole, benzimidazole, pyrimidone, substituted and unsubstituted aryl or heteroaryl; Me, iPr, or tBu; and wherein each R3 is independently selected from: aryl, thiophene, imidazole, benzimidazole, pyrimidone, substituted and unsubstituted aryl or heteroaryl; Me, iPr, tBu, thiophene, imidazole, benzimidazole, or pyrimidone.

8. The composition of claim 1, wherein beta-lactamase inhibitor is selected from one of the following structures:

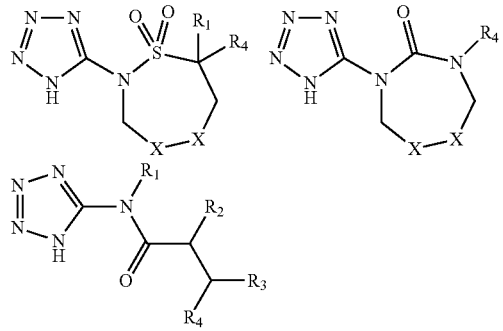

wherein each W is independently selected from: O, NO, S, SO, or SO$_2$;

wherein each R1 is independently selected from: H, Me, iPr, tBu, or other short aliphatic group, optionally substituted with F;

wherein each R2 is independently selected from: aryl, thiophene, imidazole, pyrimidone, substituted and unsubstituted aryl or heteroaryl systems; Me, iPr, or tBu;

wherein each R3 is independently selected from: aryl, thiophene, imidazole, pyrimidone, substituted and unsubstituted aryl or heteroaryl; Me, iPr, or tBu; and wherein each R4 is independently selected from: H, Me, iPr, tBu, or substituted and unsubstituted aryl or heteroaryl.

9. A pharmaceutical composition comprising a therapeutically effective amount of a beta-lactamase inhibitor, or a pharmaceutically acceptable salt of the beta-lactamase inhibitor, and a pharmaceutically acceptable carrier, to treat a condition, wherein the beta-lactamase inhibitor has one of the following structures:

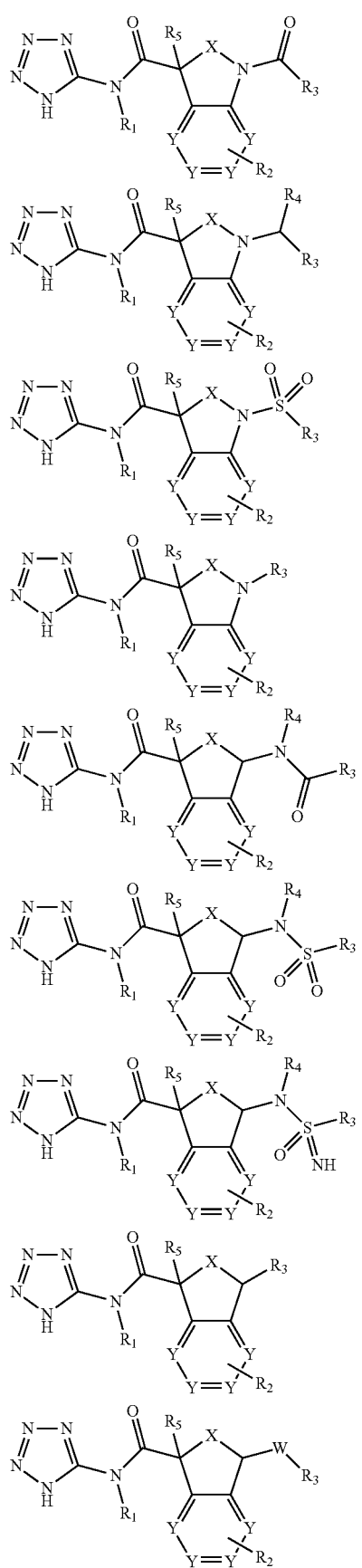
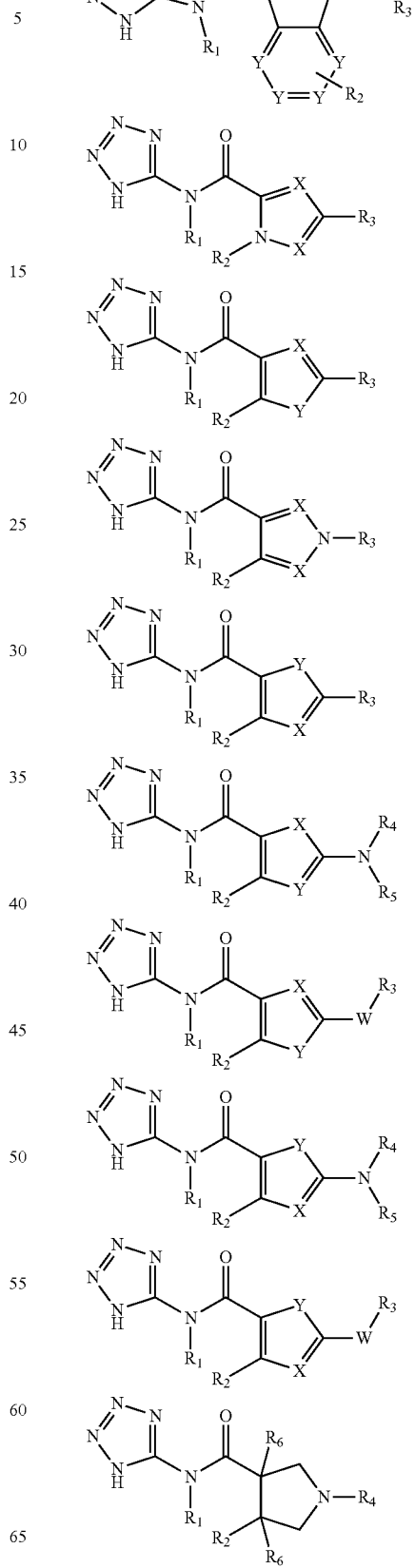

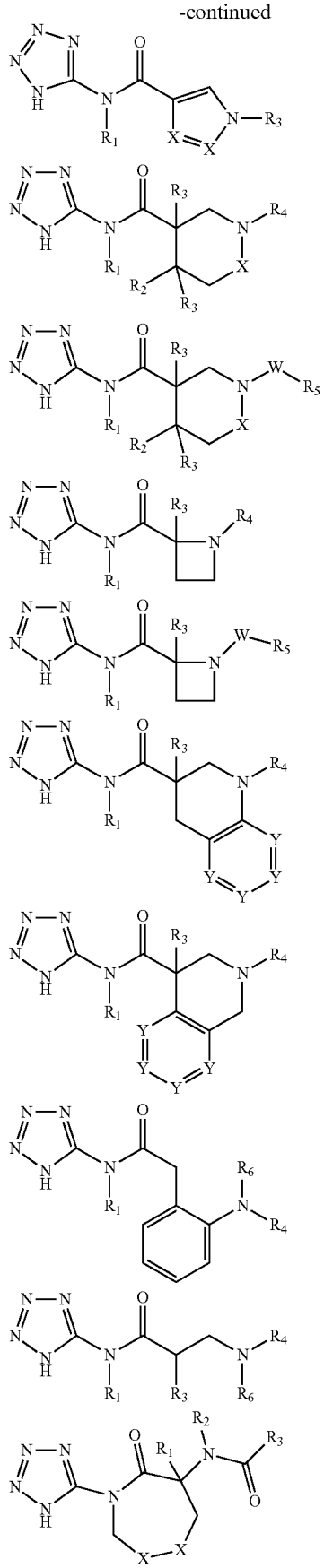
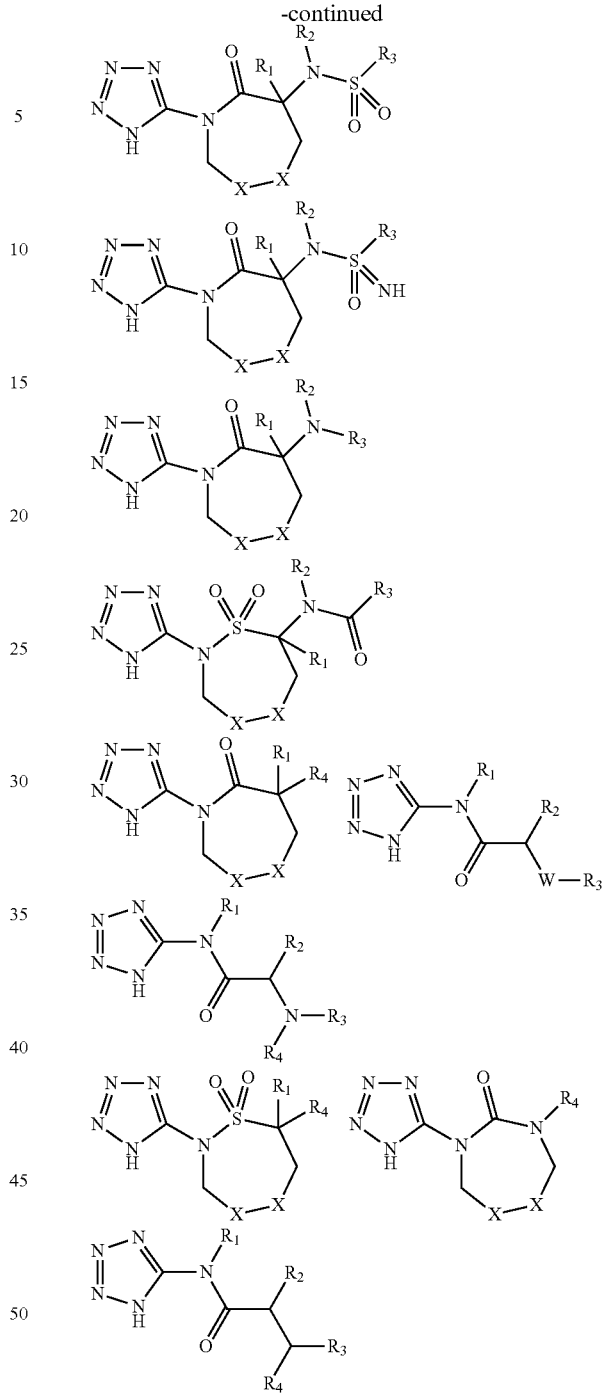

wherein each W is independently selected from: O, NO, S, SO, $CH_2$, $NMe_2$, CHMe, $C(Me)_2$, $CF_2$, or $SO_2$;

wherein X and Y are independently selected from: O, NH, NO, NMe, $NMe_2$, S, SO, $SO_2$, $CF_2$, C(=O), CH, N, CR2, $(CH_2)_n$, where n=1 or 2, a bond, or $CMe_2$ or wherein X—Y is selected from: CH=CH, cyclopropyl, or $(CH_2)_n$, where n=1 or 2;

wherein each R1 is independently selected from: H, a halogen, Me, iPr, tBu, or, optionally substituted aryl or heteroaryl;

wherein each R2 is independently selected from: H, a halogen $CH_3$, optionally substituted alkyl group, or optionally substituted aryl or heteroaryl group, OMe, NH$_2$, N(Me)$_2$, or an alkyl substituted amine;

wherein each R3 is independently selected from: H, aryl, thiophene, imidazole, pyrimidone, optionally substituted aryl or heteroaryl, Me, iPr, tBu, benzylic aryl, thiophene, imidazole, or pyrimidone;

wherein each R4 is independently selected from: H, Me, iPr, tBu, substituted and unsubstituted aryl or heteroaryl, aryl, thiophene, imidazole, or pyrimidone;

wherein each R5 is independently selected from: H, F, Me, iPr, tBu, optionally substituted aryl or heteroaryl, aryl, thiophene, imidazole, or; and wherein each R6 is independently selected from: H, Me, iPr, tBu, and substituted or unsubstituted aryl or heteroaryl.

10. The pharmaceutical composition of claim 1, further comprising an antibiotic.

11. The pharmaceutical composition of claim 10, wherein the antibiotic is a beta-lactam antibiotic.

12. The pharmaceutical of claim 9, wherein beta-lactamase inhibitor is selected from one of the following structures:

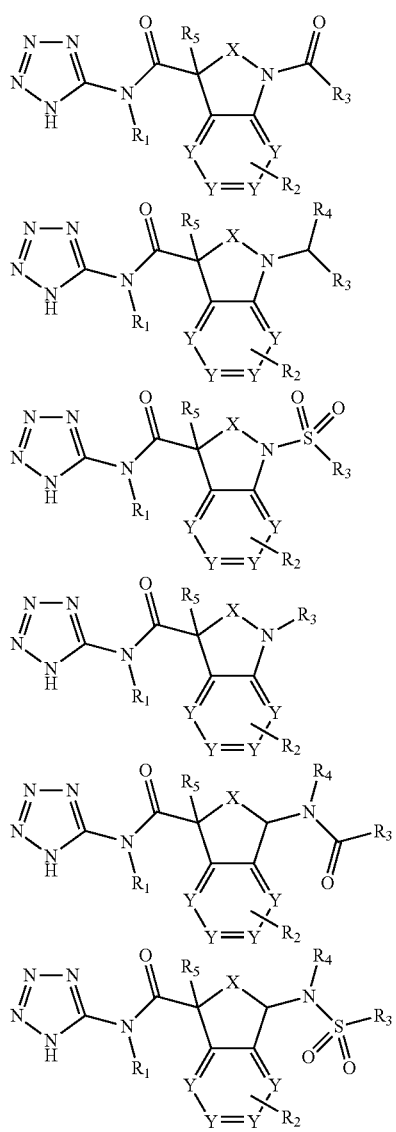

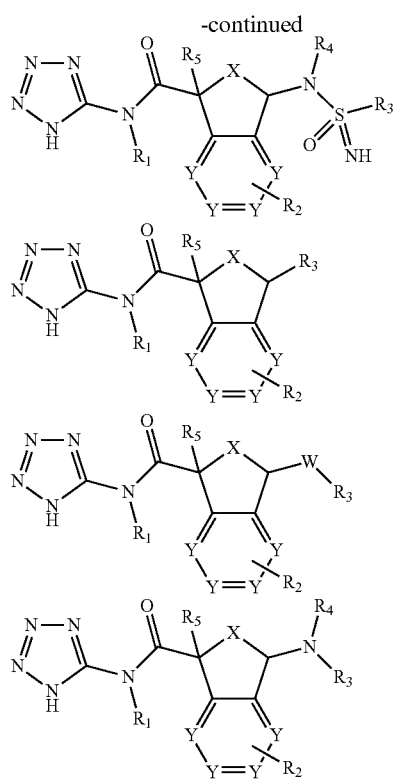

wherein each W is independently selected from: O, NO, S, SO, or SO$_2$;

wherein each X is independently selected from: O, NH, NO, NMe, S, SO, SO$_2$, C(=O), CF$_2$, CMe$_2$, or (CH$_2$)$_n$, where n=1 or 2;

wherein each Y is independently selected from: CH, N, CR2, or NO;

wherein, each R1 is independently selected from H, Me, iPr, or tBu;

wherein each R2 is independently selected from: H, F, CH$_3$, OMe, NH$_2$; N(Me)$_2$, or an alkyl substituted amine;

wherein each R3 is independently selected from: H, aryl, thiophene, imidazole, benzimidazole, pyrimidone, substituted aryl or heteroaryl, Me, iPr, or tBu;

wherein each R4 is independently selected from: H, Me, iPr, tBu, and substituted or unsubstituted aryl or heteroaryl; and wherein each R5 is independently selected from: H, a halogen, F, Me, and substituted or unsubstituted aryl or heteroaryl.

13. The pharmaceutical of claim 9, wherein beta-lactamase inhibitor is selected from one of the following structures:

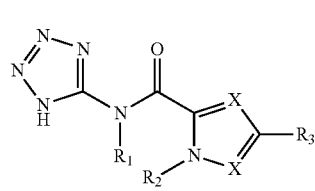

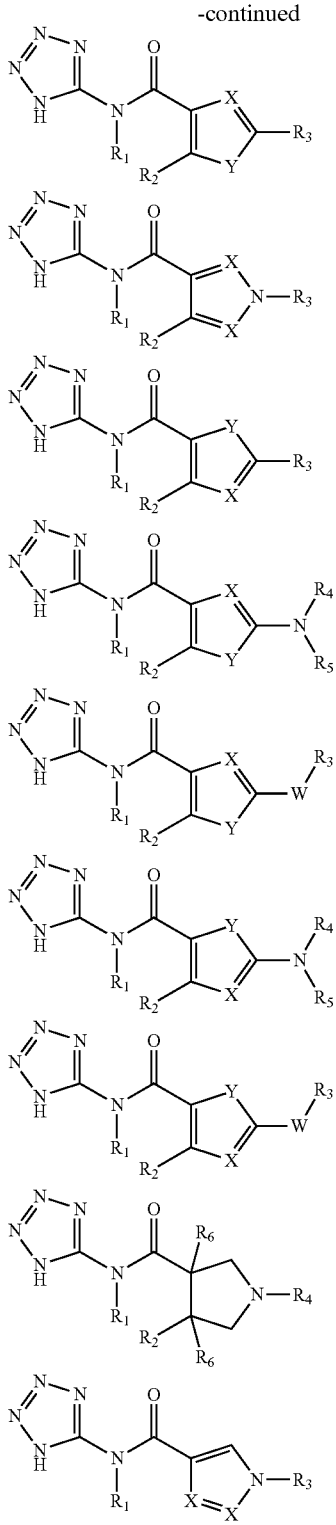

wherein each W is independently selected from: CH$_2$, O, S, SO, SO$_2$, NO, or NMe$_2$;

wherein each X is independently selected from: CH or N;

wherein each Y is independently selected from: O, S, SO, SO$_2$, NH, NO, or NMe;

wherein each R1 is independently selected from: H, Me, iPr, and tBu;

wherein each R2 is independently selected from: aryl, thiophene, imidazole, pyrimidone, substituted and unsubstituted aryl or heteroaryl; Me, iPr, tBu, thiophene, imidazole, and pyrimidone;

wherein each R3 is independently selected from: aryl, thiophene, imidazole, pyrimidone, substituted and unsubstituted aryl or heteroaryl systems; Me, iPr, tBu, thiophene, imidazole, or pyrimidone;

wherein each R4 is independently selected from: aryl, thiophene, imidazole, pyrimidone, substituted and unsubstituted aryl or heteroaryl systems; Me, iPr, tBu, thiophene, imidazole, pyrimidone;

wherein each R5 is independently selected from: H, Me, iPr, tBu, or substituted and unsubstituted aryl or heteroaryl systems; and wherein each R6 is independently selected from: H, F, Me, or substituted and unsubstituted aryl or heteroaryl systems.

14. The pharmaceutical of claim 9, wherein beta-lactamase inhibitor is selected from one of the following structures:

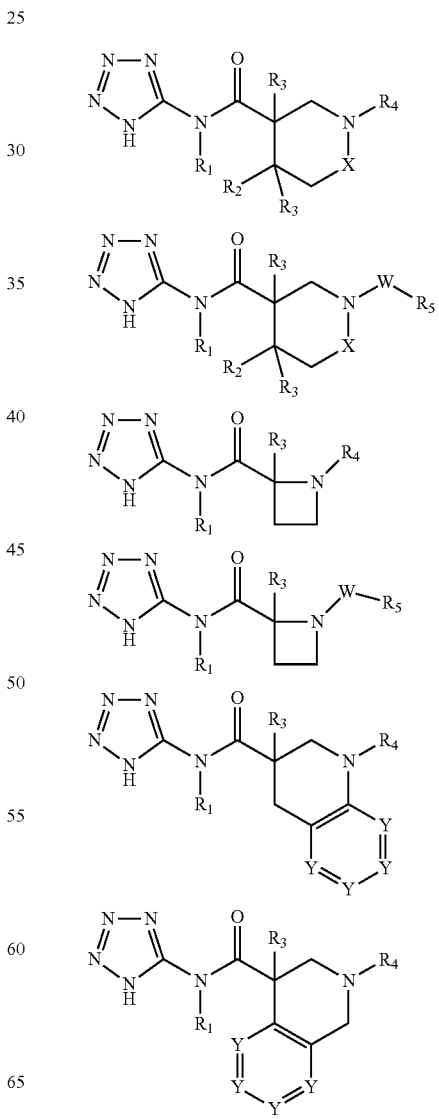

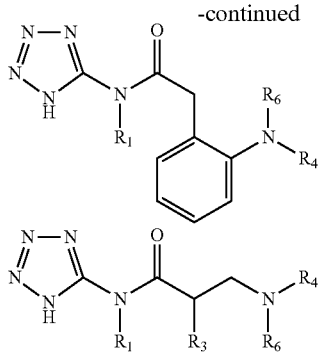

wherein each W is independently selected from: $CH_2$, CHMe, $C(Me)_2$, or $CF_2$;

wherein each X is independently a bond or $(CH_2)_n$, where n=1 or 2;

wherein each Y is independently selected from CH, N, or NO;

wherein each R1 is independently selected from: H, Me, iPr, tBu, or other short aliphatic fluorocarbons;

wherein each R2 is independently selected from: H, aryl, thiophene, imidazole, pyrimidone, substituted and unsubstituted aryl or heteroaryl; Me, iPr, tBu, thiophene, imidazole, or pyrimidone;

wherein each R3 is independently selected from: H, F, Me, or substituted and unsubstituted aryl or heteroaryl;

wherein each R4 is independently selected from: H, aryl, thiophene, imidazole, pyrimidone, substituted and unsubstituted aryl or heteroaryl; Me, iPr, tBu, thiophene, imidazole, or pyrimidone;

wherein each R5 is independently selected from: aryl, thiophene, imidazole, pyrimidone, substituted and unsubstituted aryl or heteroaryl; Me, iPr, tBu, thiophene, imidazole, or pyrimidone; and wherein each R6 is independently selected from: H, Me, iPr, tBu, or substituted and unsubstituted aryl or heteroaryl.

15. The pharmaceutical of claim 9, wherein beta-lactamase inhibitor is selected from one of the following structures:

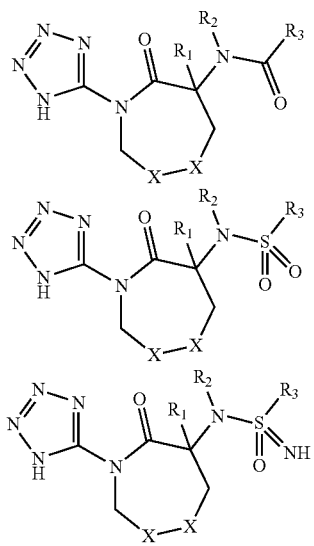

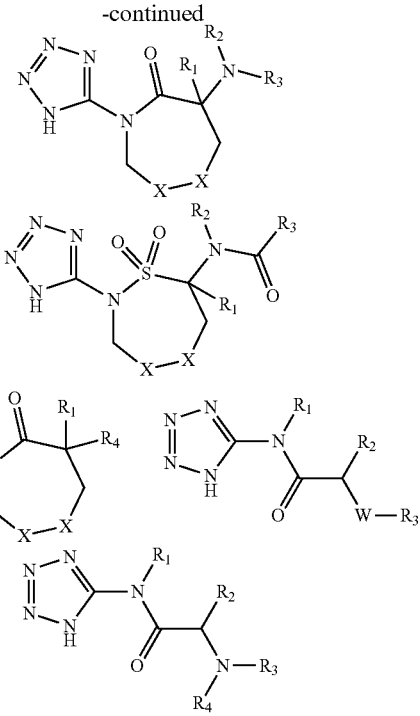

wherein X and Y are independently selected from: O, NH, NO, NMe, $NMe_2$, S, SO, $SO_2$, $CF_2$, $CH_2$, or $CMe_2$ or wherein X—Y is selected from: CH=CH, cyclopropyl, or $(CH_2)_n$, where n=1 or 2;

wherein each R1 is independently selected from: H, F, Me, or substituted and unsubstituted aryl or heteroaryl;

wherein each R2 is independently be selected from: H, Me, iPr, tBu, substituted and unsubstituted aryl or heteroaryl; and wherein each R3 is independently selected from: aryl, thiophene, imidazole, benzimidazole, pyrimidone, substituted and unsubstituted aryl or heteroaryl; Me, iPr, or tBu; and wherein each R3 is independently selected from: aryl, thiophene, imidazole, benzimidazole, pyrimidone, substituted and unsubstituted aryl or heteroaryl; Me, iPr, tBu, thiophene, imidazole, benzimidazole, or pyrimidone.

16. The pharmaceutical of claim 9, wherein beta-lactamase inhibitor is selected from one of the following structures:

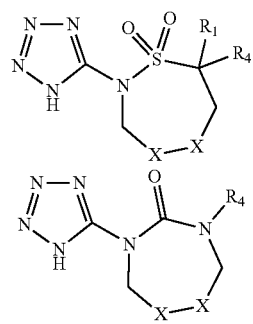

-continued

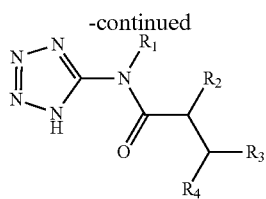

wherein each W is independently selected from: O, NO, S, SO, or $SO_2$;

wherein each R1 is independently selected from: H, Me, iPr, or tBu;

wherein each R2 is independently selected from: aryl, thiophene, imidazole, pyrimidone, substituted and unsubstituted aryl or heteroaryl; Me, iPr, or tBu;

wherein each R3 is independently selected from: aryl, thiophene, imidazole, pyrimidone, substituted and unsubstituted aryl or heteroaryl; Me, iPr, or tBu; and wherein each R4 is independently selected from: H, Me, iPr, tBu, or substituted and unsubstituted aryl or heteroaryl.

* * * * *